United States Patent
Abbot et al.

(10) Patent No.: US 10,150,816 B2
(45) Date of Patent: Dec. 11, 2018

(54) CHIMERIC ANTIGEN RECEPTORS

(71) Applicant: CELGENE CORPORATION, Summit, NJ (US)

(72) Inventors: Stewart Abbot, Warren, NJ (US); Bitao Liang, Closter, NJ (US); Tianjian Li, Belle Mead, NJ (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 14/653,650

(22) PCT Filed: Dec. 19, 2013

(86) PCT No.: PCT/US2013/076486
§ 371 (c)(1),
(2) Date: Jun. 18, 2015

(87) PCT Pub. No.: WO2014/100385
PCT Pub. Date: Jun. 26, 2014

(65) Prior Publication Data
US 2015/0307623 A1 Oct. 29, 2015

Related U.S. Application Data

(60) Provisional application No. 61/740,113, filed on Dec. 20, 2012, provisional application No. 61/779,925, filed on Mar. 13, 2013.

(51) Int. Cl.
C07K 16/28 (2006.01)
C07K 16/30 (2006.01)
C07K 14/705 (2006.01)
C07K 14/725 (2006.01)

(52) U.S. Cl.
CPC ...... C07K 16/3069 (2013.01); C07K 14/7051 (2013.01); C07K 14/70503 (2013.01); C07K 14/70521 (2013.01); C07K 16/2803 (2013.01); C07K 16/30 (2013.01); C07K 16/3061 (2013.01); C07K 2317/622 (2013.01); C07K 2319/00 (2013.01); C07K 2319/03 (2013.01); C07K 2319/33 (2013.01)

(58) Field of Classification Search
CPC ............ C07K 2319/33; C07K 2319/00; C07K 2319/03
See application file for complete search history.

(56) References Cited

U.S. PATENT DOCUMENTS

| | | | |
|---|---|---|---|
| 5,665,577 A | 9/1997 | Sodroski et al. | |
| 5,698,520 A * | 12/1997 | Honjo | C07K 14/70503 514/18.9 |
| 5,948,893 A | 9/1999 | June et al. | |
| 5,977,318 A | 11/1999 | Linsley et al. | |
| 5,994,136 A | 11/1999 | Naldini et al. | |
| 6,165,782 A | 12/2000 | Naldini et al. | |
| 6,352,694 B1 | 3/2002 | June et al. | |
| 6,428,953 B1 | 8/2002 | Naldini et al. | |
| 6,534,055 B1 | 3/2003 | June et al. | |
| 6,692,964 B1 | 2/2004 | June et al. | |
| 6,887,466 B2 | 5/2005 | June et al. | |
| 6,905,681 B1 | 6/2005 | June et al. | |
| 7,083,981 B2 | 8/2006 | Naldini et al. | |
| 7,250,299 B1 | 7/2007 | Naldini et al. | |
| 7,741,465 B1 | 6/2010 | Eshhar et al. | |
| 2003/0105000 A1* | 6/2003 | Pero | A61K 38/06 514/19.3 |
| 2011/0229461 A1* | 9/2011 | Tyson | C07K 16/2818 424/133.1 |
| 2012/0093842 A1 | 4/2012 | Eshhar et al. | |

FOREIGN PATENT DOCUMENTS

| | | |
|---|---|---|
| JP | A 2003-500021 | 1/2003 |
| WO | WO 96/05309 | 2/1996 |
| WO | WO 1996/23814 A1 | 8/1996 |
| WO | WO 00/63373 | 10/2000 |
| WO | WO 02/33101 | 4/2002 |
| WO | WO 2012/079000 A1 | 6/2012 |
| WO | WO 2014/145252 | 9/2014 |

OTHER PUBLICATIONS

Bedzyk et al. (J. Biol. Chem. Oct. 25, 1990, 265 (30): 18615-18620).*
Harper et al. (J. Immunology Aug. 1, 1991 147(3):1037-1044).*
Rudikoff et al. (PNAS, USA, 1982, 79: 1979-1983).*
Abaza et al. (Journal of Protein Chemistry, vol. 11, No. 5, 1992, pp. 433-444).*
Burgess et al. (J. of Cell Biol. 111:2129-2138, 1990).*
Ibragimova and Wade (Biophysical Journal, Oct. 1999, vol. 77, pp. 2191-2198).*
Sjoukje J. C. van der Stegen et al. (Nature Reviews Drug Discovery Jul. 2015, 14:499-509).*
Shin et al., 2012 "Positive conversion of negative signaling of CTLA4 potentiates antitumor efficacy of adoptive T-cell therapy in murine tumor models," Blood 119(24):5678-5687.
Fedorov et al., 2013, "PD-1- and CTLA-4-based inhibitory chimeric antigen receptors (iCARs) divert off-target immunotherapy responses," Sci. Transl. Med. 5(215):1-13.
Written Opinion and International Search Report dated Mar. 6, 2014 of PCT Application No. PCT/US2013/076486 filed Dec. 19, 2013 (WO 2014/100385).

(Continued)

Primary Examiner — Peter J Reddig
(74) Attorney, Agent, or Firm — Jones Day

(57) ABSTRACT

Provided herein are therapeutic polypeptides, e.g., chimeric antigen receptors, able to direct an immune cell, e.g., a T lymphocyte to a target antigen, and able to cause the T cell to proliferate or to kill cells displaying the antigen when the antigen binds to the polypeptide, wherein the polypeptides comprise a transmembrane domain from a T cell co-inhibitory protein such as CTLA4 or PD-1. Also provided herein are T lymphocytes expressing the polypeptides, and use of such T lymphocytes to treat diseases such as cancer.

10 Claims, 11 Drawing Sheets

Specification includes a Sequence Listing.

(56) References Cited

OTHER PUBLICATIONS

EP Extended Search Report and Search Opinion dated Jun. 8, 2016 for EP Application No. 13865885.1.

Fitzer-Attas et al., "Harnessing Syk family tyrosine kinases as signaling domains for chimeric single chain of the variable domain receptors: optimal design for T cell activation," J. Immunol., 1998, pp. 145-154, vol. 160(1), The American Association of Immunologists, Inc., Rockville, MD, USA.

Hyrup and Nielsen, "Peptide nucleic acids (PNA): synthesis, properties and potential applications," Bloorg. & Med. Chem., 1996, pp. 5-23, vol. 4(1).

Lázár-Molnár et al., "Crystal structure of the complex between programmed death-1 (PD-1) and its ligand PD-L2," Proc. Natl. Acad. Sci. U S A., 2008, pp. 10483-10488, vol. 105(30), The National Academy of Sciences of the USA.

Shi et al., "Chimeric antigen receptor for adoptive immunotherapy of cancer: latest research and future prospects," Mol. Cancer, 2014, pp. 1-8, vol. 13—Issue 219.

Straathof et al., "An inducible caspase 9 safety switch for T-cell therapy," Blood, 2005, pp. 4247-4254, vol. 105(11), The American Society of Hematology.

Summerton and Weller, "Morpholino antisense oligomers: design, preparation, and properties," Antisense Nucleic Acid Drug Dev., 1997, pp. 187-195, vol. 7(3).

Dobson et al., "The human transmembrane proteome," Biol. Direct., 2015, 10:31, pp. 1-18.

\* cited by examiner

CHIMERIC ANTIGEN RECEPTORS

This application is a national stage entry of International Patent Application No. PCT/US2013/076486, filed Dec. 19, 2013, which claims priority benefit of U.S. Provisional Patent Application No. 61/740,113, filed Dec, 20, 2012, and U.S. Provisional Patent Application No. 61/779,925, filed Mar. 13, 2013, the disclosure of each of which is incorporated herein by reference in its entirety.

SEQUENCE LISTING

The content of the following submission on ASCII text file is incorporated herein by reference in its entirety: a computer readable form (CRF) of the Sequence Listing, entitled 12827-401-999_sequence_listing_CRF.txt, of size 4.52kilobytes, and created on Jun. 18, 2015.

1. FIELD

The disclosure herein relates to the field of immunology, and more specifically, to the modification of T lymphocytes or other immune cells.

2. BACKGROUND

Cells of the immune system such as T lymphocytes (also referred to as T cells) recognize and interact with specific antigens through receptors or receptor complexes which, upon recognition or an interaction with such antigens, cause activation of the cell. An example of such a receptor is the antigen-specific T lymphocyte receptor complex (TCR/CD3), a complex of eight proteins. The T cell receptor (TCR) is expressed on the surface of T lymphocytes. One component, CD3, which has an invariant structure, is responsible for intracellular signaling following occupancy of the TCR by ligand. The T lymphocyte receptor for antigen-CD3 complex (TCR/CD3) recognizes antigenic peptides that are presented to it by the proteins of the major histocompatibility complex (MHC). Complexes of MHC and peptide are expressed on the surface of antigen presenting cells and other T lymphocyte targets. Stimulation of the TCR/CD3 complex results in activation of the T lymphocyte and a consequent antigen-specific immune response. The TCR/CD3 complex plays a central role in the effector function and regulation of the immune system.

T lymphocytes require a second, co-stimulatory signal to become fully active. Without such a signal, T lymphocytes are either non-responsive to antigen binding to the TCR, or become anergic. Such a co-stimulatory signal, for example, is provided by CD28, a T lymphocyte protein, which interacts with CD80 and CD86 on antigen-producing cells. ICOS (Inducible COStimulator), another T lymphocyte protein, provides a co-stimulatory signal when bound to ICOS ligand. CTLA4 (cytotoxic T-Lymphocyte Antigen 4), also known as CD152, is a receptor expressed on the surface of helper T cells and CD4+ T cells, that downregulates T cell activity. Binding of CTLA4 to its cognate ligands, CD80 and CD86, results in reduced T cell activation and proliferation. PD-1 (Programmed Cell Death-1), also known as CD279, is currently understood to negatively regulate T Cell Receptor (TCR) signals, and to broadly negatively regulate immune responses.

The essential antigen-binding, signaling, and stimulatory functions of the TCR complex have been reduced by genetic recombination methods to a single polypeptide chain, generally referred to as a Chimeric Antigen Receptor (CAR). See, e.g., Eshhar, U.S. Pat. No. 7,741,465; Eshhar, U.S. Patent Application Publication No. 2012/0093842. T lymphocytes bearing such CARs are generally referred to as CAR-T lymphocytes. CARs are constructed specifically to stimulate T cell activation and proliferation in response to a specific antigen to which the CAR binds.

3. SUMMARY

In one aspect, provided herein are polypeptides, e.g., chimeric antigen receptors (see, e.g., Eshhar, U.S. Pat. No. 7,741,465), that can be expressed by immune system cells, e.g., T lymphocytes (T cells), are membrane-bound in such immune system cells, and which comprise a transmembrane domain from an immune system protein that normally transmits an inhibitory signal to such immune system cells, e.g., a transmembrane domain from CTLA4 (Cytotoxic T-Lymphocyte Antigen 4 or Cytotoxic T-Lymphocyte Associated protein 4) or PD-1 (Programmed Cell Death-1).

In one embodiment, provided herein is a polypeptide comprising (i) a transmembrane domain comprising the transmembrane domain from CTLA4 (e.g., GenBank Accession No. NM_005214.4 (CTLA4 cytotoxic T-lymphocyte-associated protein 4 (*Homo sapiens*); Gene ID: 1493)) or PD-1 (e.g., GenBank Accession No. NM_005018.2 (programmed cell death 1 (*Homo sapiens*); Gene ID: 5133)), or a portion thereof, (ii) an intracellular domain (e.g., cytoplasmic domain) of an endogenous protein expressed on the surface of lymphocytes that triggers the activation and/or proliferation of said lymphocytes, and (iii) an extracellular domain that binds to an antigen of interest, wherein if the transmembrane domain is from CTLA4, the intracellular domain and extracellular domain of said polypeptide are not from CTLA4; and if the transmembrane domain is from PD-1, the intracellular domain and extracellular domain of said polypeptide are not from PD-1. In a specific embodiment, the polypeptide is a chimeric antigen receptor (CAR). In a specific embodiment, a T lymphocyte expressing said polypeptide, or any of such polypeptides described herein, is activated or stimulated to proliferate when said polypeptide binds to said antigen. In a specific embodiment, the polypeptide, when expressed on the surface of a T lymphocyte, directs the T lymphocyte to kill a cell expressing said antigen.

In a specific embodiment, provided herein is a polypeptide comprising a transmembrane domain from CTLA4, wherein the CTLA4 transmembrane domain is the polypeptide sequence encoded by exon 3 of a human ctla4 gene (e.g., GenBank Accession No. NM_005214.4 (CTLA4 cytotoxic T-lymphocyte-associated protein 4 (*Homo sapiens*); Gene ID: 1493)).

In another specific embodiment, the CTLA4 transmembrane domain of a polypeptide provided herein is or comprises the amino acid sequence

```
                                          (SEQ ID NO: 1)
PEPCPDSDFLLWILAAVSSGLFFYSFLLTAVSLSKM (in three-letter code, Pro-Glu-Pro-Cys-Pro-Asp- Ser-Asp-Phe-Leu-Leu-Trp-Ile-Leu-Ala-Ala-Val-Ser- Ser-Gly-Leu-Phe-Phe-Tyr-Ser-Phe-Leu-Leu-Thr-Ala- Val-Ser-Leu-Ser-Lys-Met).
```

In another specific embodiment, the CTLA4 transmembrane domain of a polypeptide provided herein is or comprises the polypeptide sequence encoded by nucleotides 610-722 of GenBank Accession No. NM_005214.4 (CTLA4 cytotoxic T-lymphocyte-associated protein 4 (*Homo sapiens*); Gene ID: 1493).

In another specific embodiment, the CTLA4 transmembrane domain of a polypeptide provided herein is or comprises the amino acid sequence (SEQ ID NO: 2)
PDSDFLLWILAAVSSGLFFYSFLLTAVSL (in three-letter code, Pro-Asp-Ser-Asp-Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val-Ser-Leu).

In another specific embodiment, the CTLA4 transmembrane domain of a polypeptide provided herein is or comprises the polypeptide sequence encoded by nucleotides 636-699 of GenBank Accession No. NM_005214.4 (CTLA4 cytotoxic T-lymphocyte-associated protein 4 (*Homo sapiens*); Gene ID: 1493).

In another specific embodiment, the CTLA4 transmembrane domain of a polypeptide provided herein is or comprises the amino acid sequence FLLWILAAVSSGLFFYS-FLLTAV (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val) (SEQ ID NO:3).

In another specific embodiment, the CTLA4 transmembrane domain of a polypeptide provided herein is or comprises the polypeptide sequence FLLWILAAVSSGLFFYS-FLLT (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr) (SEQ ID NO:4).

In another specific embodiment, the CTLA4 transmembrane domain of a polypeptide provided herein is or comprises the polypeptide sequence (SEQ ID NO: 5)
FLLWILVAVSLGLFFYSFLVSAVSLS (in three-letter code, Phe-Leu-Leu-Trp-Ile-Leu-Val-Ala-Val-Ser-Leu-Gly-Leu-Phe-Phe-Tyr-Ser-Phe-Leu-Val-Ser-Ala-Val-Ser-Leu-Ser).

In another specific embodiment, the CTLA4 transmembrane domain of a polypeptide provided herein is or comprises the polypeptide sequence (SEQ ID NO: 9)
LGIGNGTQIYVIDPEPSPDSDFLLWILAAVSSGLFFYSFLLT
AVSLSKM (in three-letter code, Leu Gly Ile Gly Asn Gly Thr Gln Ile Tyr Val Ile Asp Pro Glu Pro Ser Pro Asp Ser Asp Phe Leu Leu Trp Ile Leu Ala Ala Val Ser Ser Gly Leu Phe Phe Tyr Ser Phe Leu Leu Thr Ala Val Ser Leu Ser Lys Met).

In another specific embodiment, the CTLA4 transmembrane domain of a polypeptide provided herein is or comprises the polypeptide sequence (SEQ ID NO: 10)
FLLWILAAVSSGLFFYSFLLTAVSLSKM (in three-letter code, Phe Leu Leu Trp Ile Leu Ala Ala Val Ser Ser Gly Leu Phe Phe Tyr Ser Phe Leu Leu Thr Ala Val Ser Leu Ser Lys Met).

In another specific embodiment, the PD-1 transmembrane domain of a polypeptide provided herein is or comprises the amino acid sequence (SEQ ID NO: 6)
TLVVGVVGGLLGSLVLLVWVLAVICSRAA (in three-letter code, Thr-Leu-Val-Val-Gly-Val-Val-Gly-Gly-Leu-Leu-Gly-Ser-Leu-Val-Leu-Leu-Val-Trp-Val-Leu-Ala-Val-Ile-Cys-Ser-Arg-Ala-Ala).

In another specific embodiment, the PD-1 transmembrane domain of a polypeptide provided herein is or comprises the amino acid sequence VGVVGGLLGSLVLLVWVLAVI (in three-letter code, Val-Gly-Val-Val-Gly-Gly-Leu-Leu-Gly-Ser-Leu-Val-Leu-Leu-Val-Trp-Val-Leu-Ala-Val-Ile) (SEQ ID NO:7).

In another specific embodiment, the PD-1 transmembrane domain of a polypeptide provided herein is or comprises the amino acid sequence (SEQ ID NO: 8)
FQTLVVGVVGGLLGSLVLLVWVLAVI (in three-letter code, Phe-Glu-Thr-Leu-Val-Val-Gly-Val-Val-Gly-Gly-Leu-Leu-Gly-Ser-Leu-Val-Leu-Leu-Val-Trp-Val-Leu-Ala-Val-Ile).

In another specific embodiment, the PD-1 transmembrane domain of a polypeptide provided herein is or comprises the polypeptide sequence (SEQ ID NO: 11)
FQTLVVGVVGGLLGSLVLLVWVLAVICSRAA (in three-letter code, Phe Gln Thr Leu Val Val Gly Val Val Gly Gly Leu Leu Gly Ser Leu Val Leu Leu Val Trp Val Leu Ala Val Ile Cys Ser Arg Ala Ala).

As exemplified by the CTLA-4 and PD-1 transmembrane domain sequences described herein (i.e., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11), the transmembrane domains described herein, in certain embodiments, comprise one or more amino acids from the extracellular domain and/or one or more amino acids from the intracellular domain of the protein from which they are derived (i.e., CTLA-4 or PD-1). In certain embodiments, the transmembrane domains described herein comprise 1, 2, 3, 4, 5, 6, 7, 8, 9, 10, 11, 12, 13, 14, 15, 16, 17, 18, 19, 20, 21, 22, 23, 24, or 25 amino acids from the extracellular domain of the protein from which they are derived (i.e., CTLA-4 or PD-1). In certain embodiments, the transmembrane domains described herein comprise 1, 2, 3, 4, 5, 6, 7, 8, 9, 10, 11, 12, 13, 14, 15, 16, 17, 18, 19, 20, 21, 22, 23, 24, or 25 amino acids from the intracellular domain of the protein from which they are derived (i.e., CTLA-4 or PD-1). In certain embodiments, the transmembrane domains described herein comprise (i) 1, 2, 3, 4, 5, 6, 7, 8, 9, 10, 11, 12, 13, 14, 15, 16, 17, 18, 19, 20, 21, 22, 23, 24, or 25 amino acids from the extracellular domain of the protein from which they are derived (i.e., CTLA-4 or PD-1) and (ii) 1, 2, 3, 4, 5, 6, 7, 8, 9, 10, 11, 12, 13, 14, 15, 16, 17, 18, 19, 20, 21, 22, 23, 24, or 25 amino acids from the intracellular domain of the protein from which they are derived (i.e., CTLA-4 or PD-1).

In another specific embodiment, provided herein is a polypeptide that comprises a transmembrane domain, wherein the transmembrane domain is or comprises at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a polypeptide that comprises a transmembrane domain, wherein the transmembrane domain is at least 75%, at least 80%, at least 85%, at least 90%, or at least 95%, identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, the polypeptides provided herein comprise 1, 2, 3, 4, or 5 amino mutations, e.g., conservative amino acid mutations (e.g., hydrophobic amino acid mutated to a different hydrophobic amino acid), in the transmembrane domain of the polypeptide.

In certain embodiments, provided herein is a nucleotide sequence that encodes one of the polypeptides disclosed herein. In a specific embodiment, provided herein is a nucleotide sequence that comprises a nucleotide sequence that encodes any of the amino acid sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a nucleic acid that encodes a polypeptide described herein, wherein the nucleic acid comprises a nucleotide sequence that encodes at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a nucleic acid sequence that encodes a polypeptide that is at least 75%, at least 80%, at least 85%, at least 90%, or at least 95%, identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In certain embodiments, the extracellular domain of any of the polypeptides described herein comprises a receptor, or a portion of a receptor, that binds to an antigen. The extracellular domain may be, e.g., a receptor, or a portion of a receptor, that binds to said antigen. In certain embodiments, the extracellular domain comprises, or is, an antibody or an antigen-binding portion thereof. In a specific embodiment, the extracellular domain comprises, or is, a single-chain Fv domain. The single-chain Fv domain can comprise, for example, a $V_L$ linked to $V_H$ by a flexible linker, wherein said $V_L$ and $V_H$ are from an antibody that binds said antigen.

The antigen to which the extracellular domain of the polypeptide binds can be any antigen of interest, e.g., an antigen on a tumor cell. The tumor cell may be, e.g., a cell in a solid tumor, or a cell of non-solid tumor, e.g., a cell of a blood cancer. In certain embodiments, the antigen is a tumor-associated antigen or a tumor-specific antigen. In a specific embodiment, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific *enolase* (NSE), placental alkaline phosphatase, synaptophysis, thyroglobulin, thyroid transcription factor-1, the dimeric form of the pyruvate kinase isoenzyme type M2 (tumor M2-PK), CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, or an abnormal p53 protein. In another specific embodiment, said tumor-associated antigen or tumor-specific antigen is integrin αvβ3 (CD61), galactin, K-Ras (V-Ki-ras2 Kirsten rat sarcoma viral oncogene), or Ral-B.

In certain embodiments, the extracellular domain of the polypeptides described herein is joined to the transmembrane domain of the polypeptide by a linker, spacer or hinge polypeptide/peptide sequence, e.g., a CH2CH3 hinge sequence or a sequence from CD8, CD28, CTLA4, or PD-1.

In certain embodiments, the intracellular domain of the polypeptides described herein is or comprises an intracellular domain of a protein that is expressed on the surface of T cells and triggers activation and/or proliferation of said T cells. In a specific embodiment, the intracellular domain is a CD3ζ intracellular signaling domain. In another specific embodiment, the intracellular domain is from a lymphocyte receptor chain, a TCR/CD3 complex protein, an Fc receptor subunit, or an IL-2 receptor subunit.

In certain embodiments, the polypeptides provided herein additionally comprise one or more co-stimulatory domains, e.g., as part of the intracellular domain of the polypeptide. The one or more co-stimulatory domains can be, or can comprise, without limitation, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or, a co-stimulatory inducible T-cell costimulatory (ICOS) polypeptide sequence.

In a specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CD28 or CTLA4 hinge polypeptide sequence; (iii) a CTLA4 or PD-1 transmembrane domain; (iv) a costimulatory domain; and (v) an intracellular signaling domain. In a specific embodiment, the antigen-binding domain of the polypeptide binds to CD19.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CH2CH3 hinge polypeptide sequence; (iii) a CTLA4 or PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CD28 hinge polypeptide sequence; (iii) a CTLA4 or PD-1 transmembrane domain; (iv) a 4-1BB costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a PD-1 hinge polypeptide sequence; (iii) a CTLA4 or PD-1 transmembrane domain; (iv) a costimulatory domain; and (v) an intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a PD-1 transmembrane domain; (iv) a CD28 costimulatory domain; and (v) a CD3ζ intracellular signaling domain.

In another aspect, provided herein are T lymphocytes, e.g., T cells, that comprise, e.g., express on their cell surface, a membrane-bound polypeptide, wherein said polypeptide comprises (i) a transmembrane domain comprising the transmembrane domain from CTLA4 or PD-1, or a portion thereof, (ii) an intracellular domain of an endogenous protein expressed on the surface of lymphocytes and that triggers the activation and/or proliferation of said lymphocytes, and (iii) an extracellular domain that binds to an antigen of interest, wherein if the transmembrane domain is from CTLA4, the intracellular domain and extracellular domain (optionally excluding a CTLA4 linker) of said polypeptide are not from CTLA4; and if the transmembrane domain is from PD-1, the intracellular domain and extracellular domain of said polypeptide are not from PD-1. In a specific embodiment, the polypeptide is a chimeric antigen receptor (CAR).

In a specific embodiment, provided herein is a T lymphocyte comprising a polypeptide that comprises a transmembrane domain from CTLA4, wherein the CTLA4 transmembrane domain is the polypeptide sequence encoded by exon 3 of a human CTLA4 gene (e.g., GenBank Accession No. NM_005214.4 (CTLA4 cytotoxic T-lymphocyte-associated protein 4 (*Homo sapiens*); Gene ID: 1493)).

In another specific embodiment, provided herein is a T lymphocyte comprising a polypeptide that comprises a transmembrane domain from CTLA4, wherein the CTLA4 transmembrane domain is or comprises the amino acid sequence (SEQ ID NO: 1)
PEPCPDSDFLLWILAAVSSGLFFYSFLLTAVSLSKM (in three-letter code, Pro-Glu-Pro-Cys-Pro-Asp- Ser-Asp-Phe-Leu-Leu-Trp-Ile-Leu-Ala-Ala-Val-Ser- Ser-Gly-Leu-Phe-Phe-Tyr-Ser-Phe-Leu-Leu-Thr-Ala- Val-Ser-Leu-Ser-Lys-Met).

In another specific embodiment, provided herein is a T lymphocyte comprising a polypeptide that comprises a transmembrane domain from CTLA4, wherein the CTLA4 transmembrane domain is or comprises the polypeptide sequence encoded by nucleotides 610-722 of GenBank Accession No. NM_005214.4 (CTLA4 cytotoxic T-lymphocyte-associated protein 4 (*Homo sapiens*); Gene ID: 1493).

In another specific embodiment, provided herein is a T lymphocyte comprising a polypeptide that comprises a transmembrane domain from CTLA4, wherein the CTLA4 transmembrane domain is or comprises the amino acid sequence (SEQ ID NO: 2)
PDSDFLLWILAAVSSGLFFYSFLLTAVSL (in three-letter code, Pro-Asp-Ser-Asp-Phe-Leu- Leu-Trp-Ile-Leu-Ala-Ala-Val-Ser-Ser-Gly-Leu- Phe-Phe-Tyr-Ser-Phe-Leu-Leu-Thr-Ala-Val-Ser-Leu).

In another specific embodiment, provided herein is a T lymphocyte comprising a polypeptide that comprises a transmembrane domain from CTLA4, wherein the CTLA4 transmembrane domain is or comprises the polypeptide sequence encoded by nucleotides 636-699 of GenBank Accession No. NM_005214.4 (CTLA4 cytotoxic T-lymphocyte-associated protein 4 (*Homo sapiens*); Gene ID: 1493).

In another specific embodiment, provided herein is a T lymphocyte comprising a polypeptide that comprises a transmembrane domain from CTLA4, wherein the CTLA4 transmembrane domain is or comprises the amino acid sequence (SEQ ID NO: 3)
FLLWILAAVSSGLFFYSFLLTAV (in three-letter code, Phe-Leu-Leu-Trp-Ile-Leu- Ala-Ala-Val-Ser-Ser-Gly-Leu-Phe-Phe-Tyr-Ser-Phe- Leu-Leu-Thr-Ala-Val).

In another specific embodiment, provided herein is a T lymphocyte comprising a polypeptide that comprises a transmembrane domain from CTLA4, wherein the CTLA4 transmembrane domain is or comprises the polypeptide sequence (SEQ ID NO: 4)
FLLWILAAVSSGLFFYSFLLT (in three-letter code, Phe-Leu-Leu-Trp-Ile-Leu- Ala-Ala-Val-Ser-Ser-Gly-Leu-Phe-Phe-Tyr-Ser-Phe- Leu-Leu-Thr).

In another specific embodiment, provided herein is a T lymphocyte comprising a polypeptide that comprises a transmembrane domain from CTLA4, wherein the CTLA4 transmembrane domain is or comprises the polypeptide sequence (SEQ ID NO: 5)
FLLWILVAVSLGLFFYSFLVSAVSLS (in three-letter code, Phe-Leu-Leu-Trp-Ile-Leu- Val-Ala-Val-Ser-Leu-Gly-Leu-Phe-Phe-Tyr-Ser-Phe- Leu-Val-Ser-Ala-Val-Ser-Leu-Ser).

In another specific embodiment, provided herein is a T lymphocyte comprising a polypeptide that comprises a transmembrane domain from CTLA4, wherein the CTLA4 transmembrane domain is or comprises the polypeptide sequence (SEQ ID NO: 9)
LGIGNGTQIYVIDPEPSPDSDFLLWILAAVSSGLFFYSFLLTA

VSLSKM (in three-letter code, Leu Gly Ile Gly Asn Gly

Thr Gln Ile Tyr Val Ile Asp Pro Glu Pro Ser Pro

Asp Ser Asp Phe Leu Leu Trp Ile Leu Ala Ala Val

Ser Ser Gly Leu Phe Phe Tyr Ser Phe Leu Leu Thr

Ala Val Ser Leu Ser Lys Met).

In another specific embodiment, provided herein is a T lymphocyte comprising a polypeptide that comprises a transmembrane domain from CTLA4, wherein the CTLA4 transmembrane domain is or comprises the polypeptide sequence (SEQ ID NO: 10)
FLLWILAAVSSGLFFYSFLLTAVSLSKM (in three-letter code, Phe Leu Leu Trp Ile Leu Ala Ala Val Ser Ser Gly Leu Phe Phe Tyr Ser Phe Leu Leu Thr Ala Val Ser Leu Ser Lys Met).

In another specific embodiment, provided herein is a T lymphocyte comprising a polypeptide that comprises a transmembrane domain from PD-1, wherein the PD-1 transmembrane domain is or comprises the polypeptide sequence (SEQ ID NO: 6)
TLVVGVVGGLLGSLVLLVWVLAVICSRAA (in three-letter code, Thr-Leu-Val-Val-Gly-Val- Val-Gly-Gly-Leu-Leu-Gly-Ser-Leu-Val-Leu-Leu-Val- Trp-Val-Leu-Ala-Val-Ile-Cys-Ser-Arg-Ala-Ala).

In another specific embodiment, provided herein is a T lymphocyte comprising a polypeptide that comprises a transmembrane domain from PD-1, wherein the PD-1 transmembrane domain is or comprises the amino acid sequence (SEQ ID NO: 7)
VGVVGGLLGSLVLLVWVLAVI (in three-letter code, Val-Gly-Val-Val-Gly-Gly- Leu-Leu-Gly-Ser-Leu-Val-Leu-Leu-Val-Trp-Val-Leu- Ala-Val-Ile).

In another specific embodiment, provided herein is a T lymphocyte comprising a polypeptide that comprises a transmembrane domain from PD-1, wherein the PD-1 transmembrane domain is or comprises the amino acid sequence (SEQ ID NO: 8)
FQTLVVGVVGGLLGSLVLLVWVLAVI (in three-letter code, Phe-Glu-Thr-Leu-Val-Val- Gly-Val-Val-Gly-Gly-Leu-Leu-Gly-Ser-Leu-Val-Leu- Leu-Val-Trp-Val-Leu-Ala-Val-Ile).

In another specific embodiment, provided herein is a T lymphocyte comprising a polypeptide that comprises a transmembrane domain from PD-1, wherein the PD-1 transmembrane domain is or comprises the amino acid sequence

```
                                                    (SEQ ID NO: 11)
FQTLVVGVVGGLLGSLVLLVWVLAVICSRAA (in three-letter code, Phe Gln Thr Leu Val Val Gly Val Val Gly Gly Leu Leu Gly Ser Leu Val Leu Leu Val Trp Val Leu Ala Val Ile Cys Ser Arg Ala Ala).
```

In certain embodiments, a nucleotide sequence expressed or encoded by a T lymphocyte provided herein (i.e., a T lymphocyte comprising a polypeptide described herein) comprises a nucleotide sequence that encodes any of the amino acid sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In another specific embodiment, provided herein is a T lymphocyte comprising a polypeptide that comprises a transmembrane domain, wherein the transmembrane domain is or comprises at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In certain embodiments, provided herein is a T lymphocyte comprising a nucleic acid that encodes a polypeptide described herein, wherein the nucleic acid comprises a nucleotide sequence that encodes at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In certain embodiments, the extracellular domain of a polypeptide expressed by the T lymphocytes provided herein comprises a receptor, or a portion of a receptor, that binds to an antigen of interest. The extracellular domain may be, e.g., a receptor, or a portion of a receptor, that binds to said antigen. In certain embodiments, the extracellular domain comprises, or is, an antibody or an antigen-binding portion thereof. In specific embodiments, the extracellular domain comprises, or is, a single-chain Fv domain. The single-chain Fv domain can comprise, for example, a V$_L$ linked to V$_H$ by a flexible linker, wherein said V$_L$ and V$_H$ are from an antibody that binds said antigen.

The antigen to which the extracellular domain of the polypeptide expressed by a T lymphocyte provided herein binds, and therefore to which the T cell is directed by the polypeptide, can be any antigen of interest, e.g., an antigen on a tumor cell. The tumor cell may be, e.g., a cell in a solid tumor, or a cell of a non-solid tumor, e.g., a cell of a blood cancer. In certain embodiments, the antigen is a tumor-associated antigen or a tumor-specific antigen. In certain embodiments, the antigen is one or more of Kappa, Lambda, CD19, CD22, CD27, CD30, CD70, GD2, HER2, CEA, EGFRvIII, Sperm Protein17, PSCA, mesothelin, PAP (prostatic acid phosphatase), prostein, TARP (T cell receptor gamma alternate reading frame protein), Trp-p8, STEAP1 (six-transmembrane epithelial antigen of the prostate 1), and/or MUC-1. In various specific embodiments, without limitation, the tumor-associated antigen or tumor-specific antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific *enolase* (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In another specific embodiment, said tumor-associated antigen or tumor-specific antigen is integrin αvβ3 (CD61), galactin, K-Ras (V-Ki-ras2 Kirsten rat sarcoma viral oncogene), or Ral-B.

In certain embodiments, the extracellular domain of a polypeptide expressed by a T lymphocyte described herein is joined to said transmembrane domain of the polypeptide by a linker, spacer or hinge polypeptide sequence, e.g., a sequence from CD8, CD28, CTLA4 or PD-1.

In certain embodiments, the intracellular domain of a polypeptide expressed by a T lymphocyte described herein is or comprises an intracellular domain of a protein that is normally expressed on the surface of T cells and which triggers activation and/or proliferation of said T cells. In a specific embodiment, the intracellular domain is a CD3ζ intracellular signaling domain. In another embodiment, the intracellular domain is from a lymphocyte receptor chain, a TCR/CD3 complex protein, an Fc receptor subunit or an IL-2 receptor subunit.

In certain embodiments, a polypeptide expressed by a T lymphocyte described herein additionally comprises one or more co-stimulatory domains, e.g., as part of the intracellular domain of the polypeptide. The one or more co-stimulatory domains can be, or comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence.

In a specific embodiment, the T lymphocytes provided herein express or comprise a polypeptide that comprises, in order, from N-terminus to C-terminus: (i) an antigen-binding domain (e.g., an antigen binding domain that binds an antigen on a tumor cell, e.g., an antigen on a tumor cell described above); (ii) a CD28 or CTLA4 hinge polypeptide sequence; (iii) a CTLA4 or PD-1 transmembrane domain; (iv) a costimulatory domain; and (v) an intracellular signaling domain. In a specific embodiment, the antigen-binding domain of the polypeptide binds to CD19.

In a specific embodiment, the T lymphocytes provided herein express or comprise a polypeptide that comprises, in order, from N-terminus to C-terminus: (i) an antigen-binding domain (e.g., an antigen binding domain that binds an antigen on a tumor cell, e.g., an antigen on a tumor cell described above); (ii) a CH2CH3 hinge polypeptide sequence; (iii) a CTLA4 or PD-1 transmembrane domain; (iv) a CD28 costimulatory domain; and (v) a CD3ζ intracellular signaling domain. In a specific embodiment, the antigen-binding domain of the polypeptide binds to HER2.

In a specific embodiment, the T lymphocytes provided herein express or comprise a polypeptide that comprises, in order, from N-terminus to C-terminus: (i) an antigen-binding domain (e.g., an antigen binding domain that binds an antigen on a tumor cell, e.g., an antigen on a tumor cell described above); (ii) a CH2CH3 hinge polypeptide sequence; (iii) a CTLA4 or PD-1 transmembrane domain; (iv) a CD28 costimulatory domain; and (v) a CD3ζ intracellular signaling domain. In a specific embodiment, the antigen-binding domain of the polypeptide binds to HER2.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a CTLA4 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a CTLA4 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a PD-1 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) an antigen-binding domain (e.g., an antigen binding domain that binds an antigen on a tumor cell, e.g., an antigen on a tumor cell described above); (ii) a PD-1 hinge polypeptide sequence; (iii) a CTLA4 or PD-1 transmembrane domain; (iv) a costimulatory domain; and (v) an intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a CTLA4 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a PD-1 transmembrane domain; (iv) a CD28 costimulatory domain; and (v) a CD3ζ intracellular signaling domain.

In a specific embodiment, the T lymphocytes provided herein that express or comprise one or more of the polypeptides provided herein, become activated or stimulated to proliferate when said polypeptide binds to the antigen to which the antigen binding domain or single-chain Fv domain of the polypeptide is specific. In another specific embodiment, the T lymphocytes provided herein that express or comprise one or more of the polypeptides provided herein, kill cells that express or comprise the antigen to which the antigen binding domain or single-chain Fv domain of the polypeptide is specific when the T lymphocytes come in contact with said antigen-expressing cells.

In another aspect, provided herein are methods of treating an individual having a disease or disorder, wherein the disease or disorder is characterized, or is characterizable, by cells expressing an antigen, comprising administering to the individual one or more of the T lymphocytes provided herein, i.e., T lymphocytes that comprise or express a polypeptide described herein.

4. BRIEF DESCRIPTION OF THE DRAWINGS

Figure 6A:
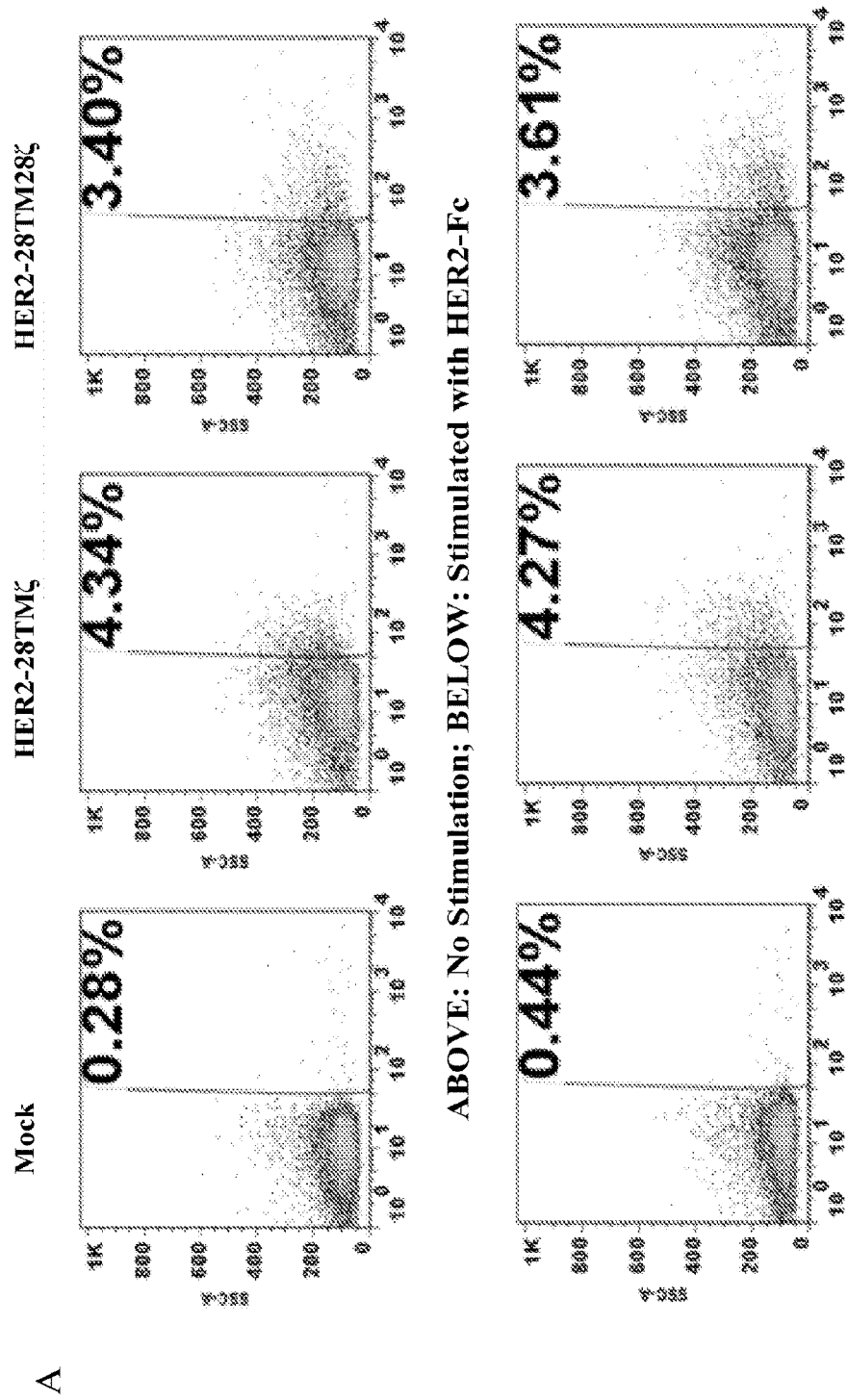
Figure 6B:
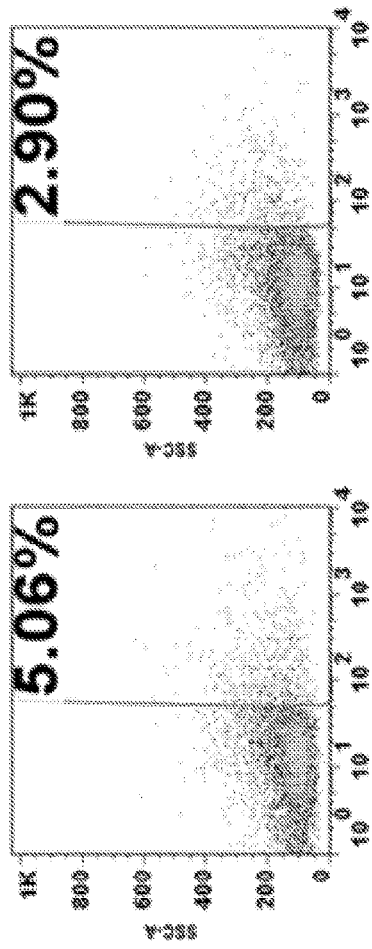
Figure 6B:
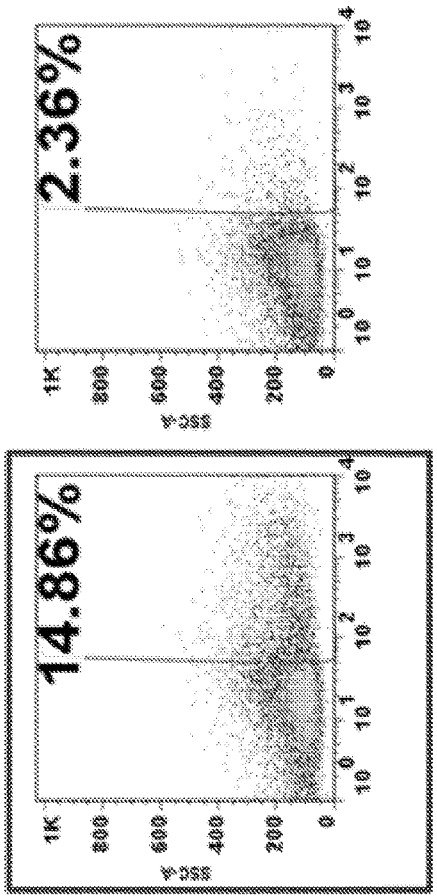

FIG. 6 depicts percentages of CAR T cells the express certain anti-HER2 CARs or a mock control in the absence (top panels) and presence (bottom panels) of stimulation with HER2-Fc. A) Percentages of anti-HER2 CAR T cells expressing Mock, HER2-28TMζ, or HER2-28TM28ζ. B) Percentages of anti-HER2 CAR T cells expressing HER2-CTLA4TM28ζ or HER2-4-1BBTM28ζ.

Figure 7:
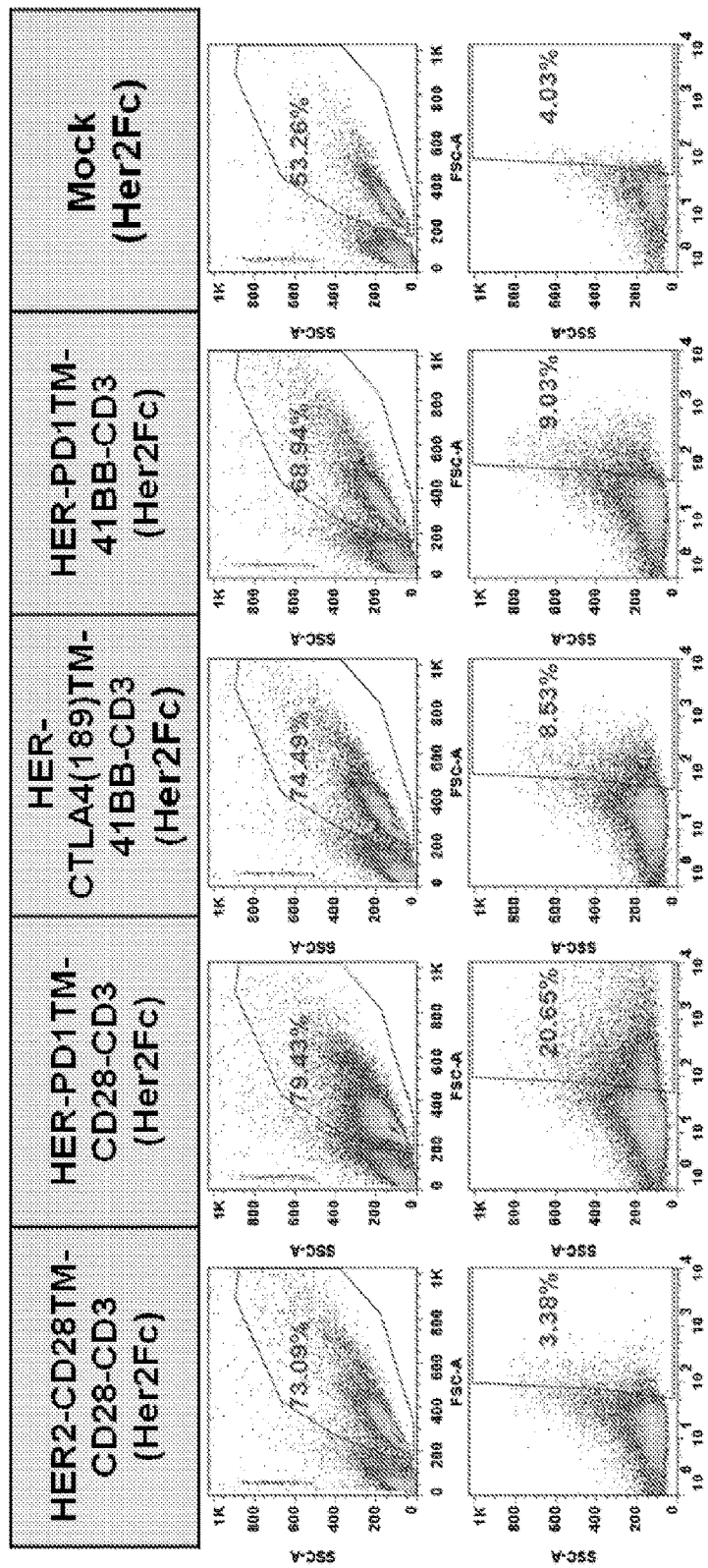

FIG. 7 depicts expression of CARs by T cells eleven days after transduction of the T cells with lentiviral vectors that express the CARS.

Figure 8:
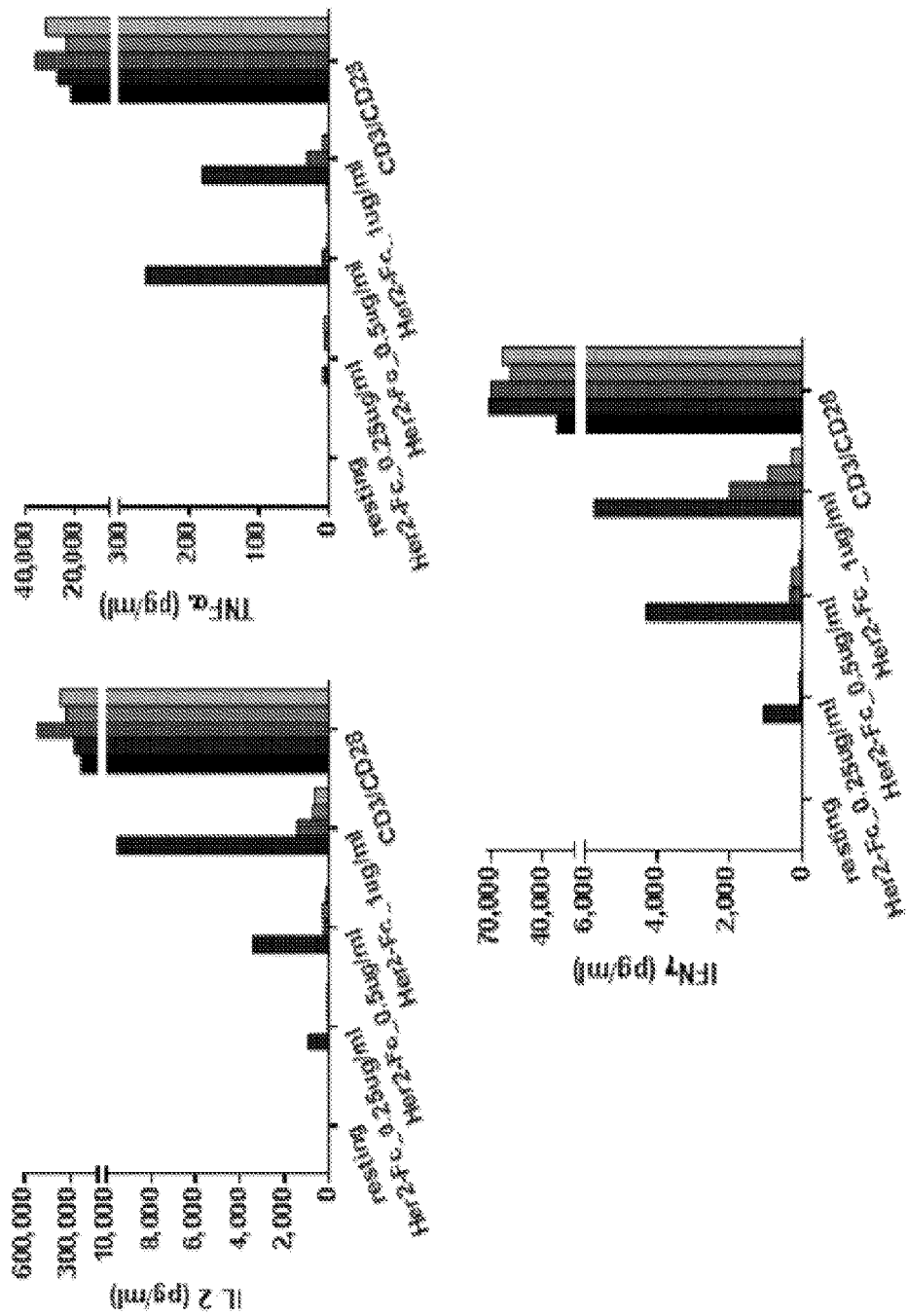

FIG. 8 depicts IL-2, TNF-α, and IFN-γ production by CAR T cells (i) in the resting state, (ii) after exposure to 0.25, 0.5, or 1.0 µg/ml HER2-Fc; or (iii) after CD3/CD28 ligation. First (leftmost) bar in each group: mock-transduced cells (no CAR expressed); second bar in each group: cells transduced with CAR designated HER-PD1TM-CD28-CD3; third bar in each group: cells transduced with CAR designated HER-CTLA4(189)TM-41BB-CD3; fourth bar in each group: cells transduced with CAR designated HER- PD1TM-41BB-CD3; fifth (rightmost) bar in each group: cells transduced with CAR designated HER2-CD28TM-CD28-CD3.

Figure 9:
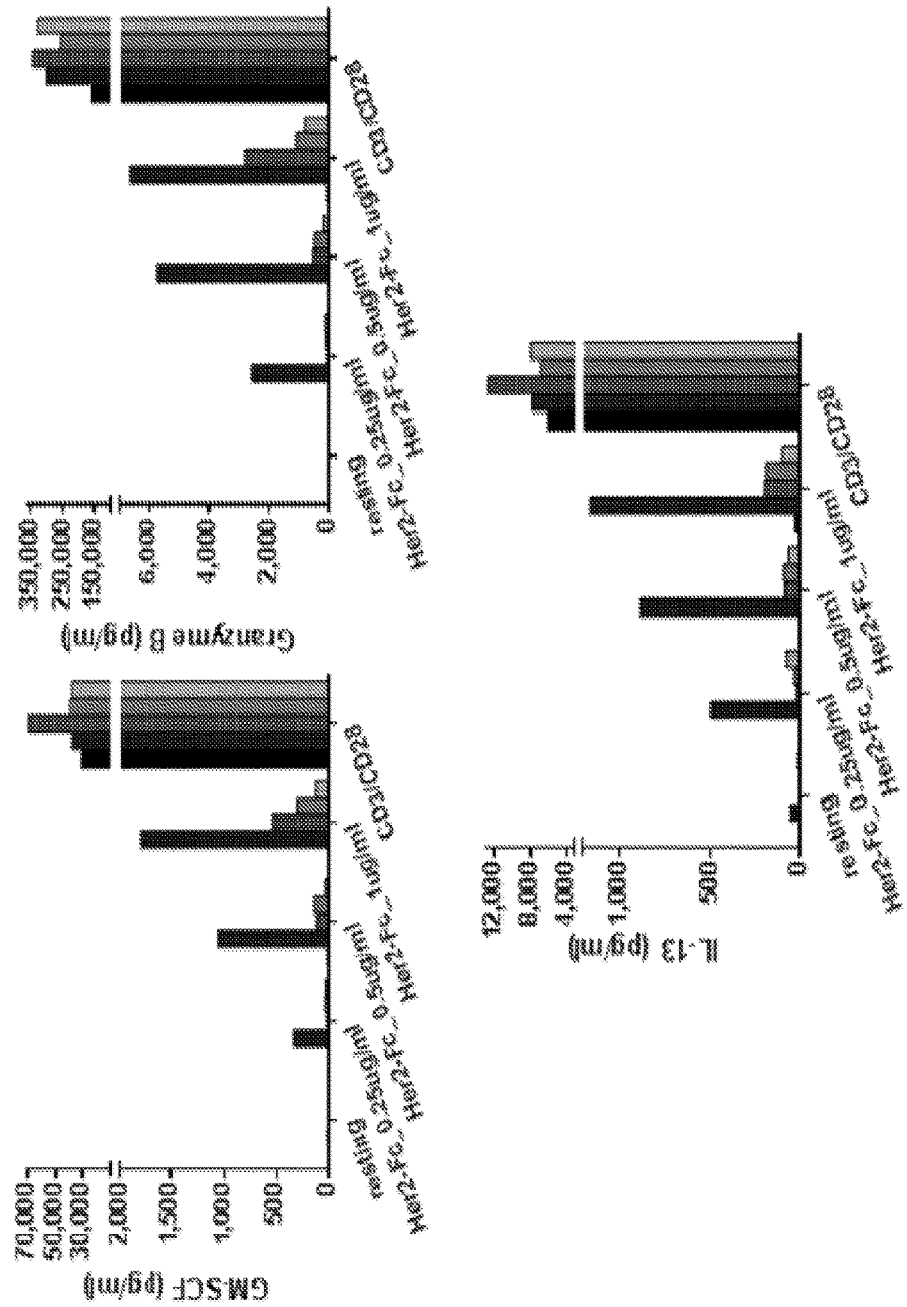

FIG. 9 depicts GM-CSF, Granzyme B, and IL-13 production by CAR T cells (i) in the resting state, (ii) after exposure to 0.25, 0.5, or 1.0 µg/ml HER2-Fc; or (iii) after CD3/CD28 ligation. First (leftmost) bar in each group: mock-transduced cells (no CAR expressed); second bar in each group: cells transduced with CAR designated HER-PD1TM-CD28-CD3; third bar in each group: cells transduced with CAR designated HER-CTLA4(189)TM-41BB-CD3; fourth bar in each group: cells transduced with CAR designated HER-PD1TM-41BB-CD3; fifth (rightmost) bar in each group: cells transduced with CAR designated HER2-CD28TM-CD28-CD3.

Figure 10:
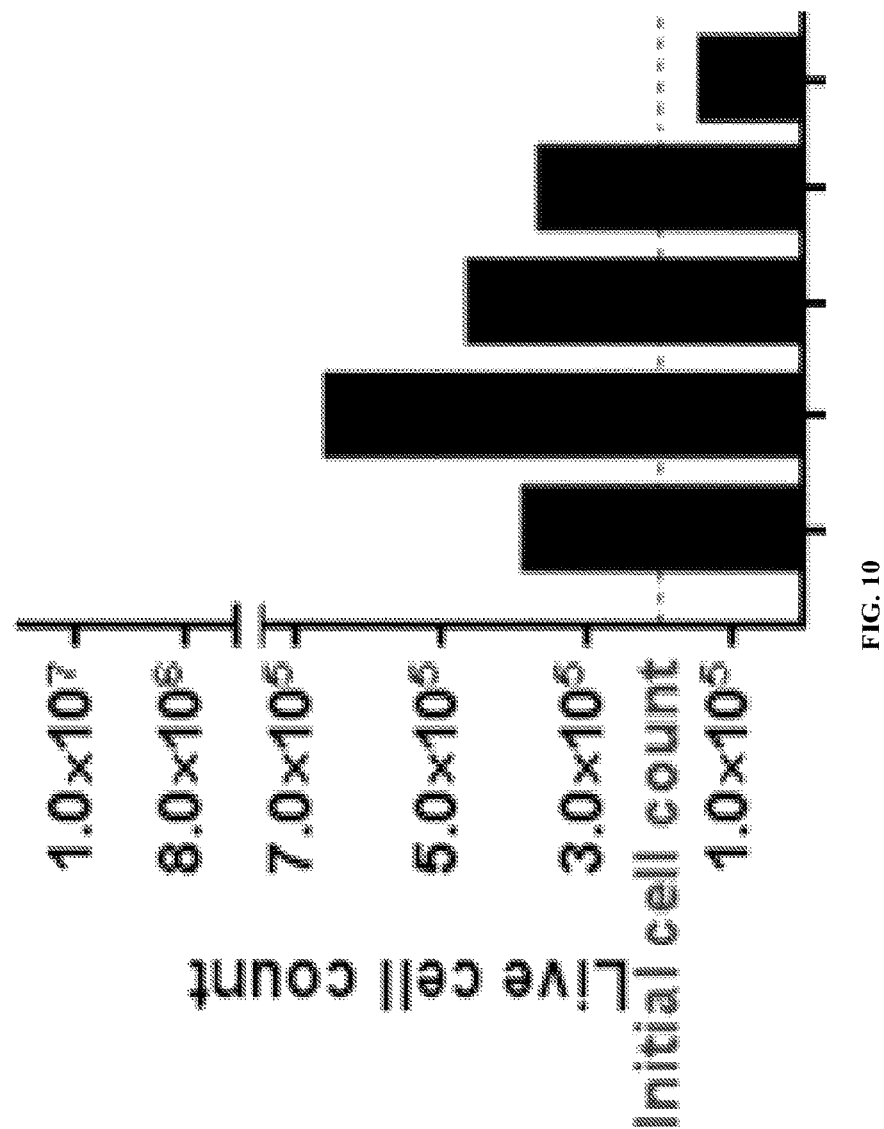

FIG. 10 depicts live T cell counts following stimulation with HER2-Fc. First (leftmost) bar: cells transduced with CAR designated HER2-CD28TM-CD28-CD3; second bar: cells transduced with CAR designated HER-PD1TM-CD28-CD3; third bar: cells transduced with CAR designated HER-CTLA4(189)TM-41BB-CD3; fourth bar: cells transduced with CAR designated HER-PD1TM-41BB-CD3; fifth (rightmost) bar: mock-transduced cells (no CAR expressed).

5. DETAILED DESCRIPTION

In one aspect, provided herein are polypeptides, e.g., chimeric antigen receptors (see, e.g., Eshhar, U.S. Pat. No. 7,741,465), that can be expressed by immune system cells, e.g., T lymphocytes (T cells), are membrane-bound in such immune system cells, and which comprise a transmembrane domain from an immune system protein that normally transmits an inhibitory signal to such immune system cells, e.g., a transmembrane domain from CTLA4 (Cytotoxic T-Lymphocyte Antigen 4 or Cytotoxic T-Lymphocyte Associated protein 4) or PD-1 (Programmed Cell Death-1). Further provided herein are nucleic acid sequences encoding the polypeptides described herein. Also provided herein are immune system cells, e.g., T lymphocytes (e.g., T cells), expressing such polypeptides.

The polypeptides provided herein comprise an extracellular domain that binds to an antigen, e.g., an antigen on a cell, a transmembrane domain, and an intracellular (cytoplasmic) signaling domain that transmits a primary activation signal to an immune cell. When the polypeptides provided herein are expressed on the surface of, e.g., a T lymphocyte, and when the extracellular domain of the CAR binds to an antigen, the intracellular signaling domain transmits a signal to the T lymphocyte to activate and/or proliferate, and, if the antigen is present on a cell surface, to kill the cell expressing the antigen. Because T lymphocytes require two signals in order to fully activate, a primary activation signal and a costimulatory signal, in certain embodiments, the polypeptides described herein can comprise a costimulatory domain such that binding of the antigen to the extracellular domain results in transmission of both a primary activation signal and a costimulatory signal.

The polypeptides, e.g., CARs, provided herein are functional, immune stimulatory polypeptides that comprise a transmembrane domain from a T cell co-inhibitory protein, e.g., CTLA4 or PD-1. In one aspect, provided herein is a polypeptide comprising (i) a transmembrane domain from CTLA4 or PD-1, (ii) an intracellular domain (e.g., cytoplasmic domain) of an endogenous protein expressed on the surface of lymphocytes and that triggers the activation and/or proliferation of said lymphocytes, and (iii) an extracellular domain that binds to an antigen, wherein if the transmembrane domain is from CTLA4, the intracellular domain and extracellular domain of said polypeptide are not from CTLA4; and if the transmembrane domain is from PD-1, the intracellular domain and extracellular domain of said polypeptide are not from PD-1. In a specific embodiment, a T lymphocyte expressing a polypeptide described herein is activated or stimulated to proliferate when said polypeptide binds to an antigen to which the polypeptide is specific (i.e., an antigen that is bound by the extracellular domain of the polypeptide). In a specific embodiment, the polypeptide, when expressed on the surface of a T lymphocyte, directs the T lymphocyte to kill a cell expressing said antigen.

In certain embodiments the polypeptides provided herein comprise a transmembrane domain from CTLA4 or PD-1, or a portion thereof, wherein the CTLA4 or PD-1 transmembrane domain is from a mammalian CTLA4 or PD-1, e.g., human, primate, or rodent, e.g., murine CTLA4 or PD-1. In a specific embodiment, the transmembrane domain does not comprise amino acids from the intracellular domain, extracellular domain, or either the intracellular or extracellular domain of CTLA4 or PD-1. Specific, non-limiting examples of CTLA4 or PD-1 transmembrane domain sequences are provided below.

In a specific embodiment, provided herein is a polypeptide comprising a transmembrane domain from CTLA4, wherein the CTLA4 transmembrane domain is the polypeptide sequence encoded by exon 3 of a human ctla4 gene (e.g., GenBank Accession No. NM_005214.4 (CTLA4 cytotoxic T-lymphocyte-associated protein 4 (*Homo sapiens*); Gene ID: 1493)).

In another specific embodiment, the CTLA4 transmembrane domain of a polypeptide provided herein is or comprises the amino acid sequence (SEQ ID NO: 1)
PEPCPDSDFLLWILAAVSSGLFFYSFLLTAVSLSKM (in three-letter code, Pro-Glu-Pro-Cys-Pro-Asp- Ser-Asp-Phe-Leu-Leu-Trp-Ile-Leu-Ala-Ala-Val-Ser- Ser-Gly-Leu-Phe-Phe-Tyr-Ser-Phe-Leu-Leu-Thr-Ala- Val-Ser-Leu-Ser-Lys-Met).

In another specific embodiment, the CTLA4 transmembrane domain of a polypeptide provided herein is or comprises the polypeptide sequence encoded by nucleotides 610-722 of GenBank Accession No. NM_005214.4 (CTLA4 cytotoxic T-lymphocyte-associated protein 4 (*Homo sapiens*); Gene ID: 1493).

In another specific embodiment, the CTLA4 transmembrane domain of a polypeptide provided herein is or comprises the amino acid sequence (SEQ ID NO: 2)
PDSDFLLWILAAVSSGLFFYSFLLTAVSL (in three-letter code, Pro-Asp-Ser-Asp-Phe-Leu- Leu-Trp-Ile-Leu-Ala-Ala-Val-Ser-Ser-Gly-Leu-Phe- Phe-Tyr-Ser-Phe-Leu-Leu-Thr-Ala-Val-Ser-Leu).

In another specific embodiment, the CTLA4 transmembrane domain of a polypeptide provided herein is or comprises the polypeptide sequence encoded by nucleotides 636-699 of GenBank Accession No. NM_005214.4 (CTLA4 cytotoxic T-lymphocyte-associated protein 4 (*Homo sapiens*); Gene ID: 1493).

In another specific embodiment, the CTLA4 transmembrane domain of a polypeptide provided herein is or comprises the amino acid sequence FLLWILAAVSSGLFFYS-FLLTAV (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val) (SEQ ID NO:3).

In another specific embodiment, the CTLA4 transmembrane domain of a polypeptide provided herein is or comprises the polypeptide sequence FLLWILAAVSSGLFFYS-FLLT (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr) (SEQ ID NO:4).

In another specific embodiment, the CTLA4 transmembrane domain of a polypeptide provided herein is or comprises the polypeptide sequence (SEQ ID NO: 5)
FLLWILVAVSLGLFFYSFLVSAVSLS (in three-letter code, Phe-Leu-Leu-Trp-Ile-Leu- Val-Ala-Val-Ser-Leu-Gly-Leu-Phe-Phe-Tyr-Ser-Phe- Leu-Val-Ser-Ala-Val-Ser-Leu-Ser).

In another specific embodiment, the CTLA4 transmembrane domain of a polypeptide provided herein is or comprises the polypeptide sequence (SEQ ID NO: 9)
LGIGNGTQIYVIDPEPSPDSDFLLWILAAVSSGLFFYS

FLLTAVSLSKM (in three-letter code, Leu Gly Ile Gly Asn Gly

Thr Gln Ile Tyr Val Ile Asp Pro Glu Pro Ser Pro

Asp Ser Asp Phe Leu Leu Trp Ile Leu Ala Ala Val

Ser Ser Gly Leu Phe Phe Tyr Ser Phe Leu Leu Thr

Ala Val Ser Leu Ser Lys Met).

In another specific embodiment, the CTLA4 transmembrane domain of a polypeptide provided herein is or comprises the polypeptide sequence (SEQ ID NO: 10)
FLLWILAAVSSGLFFYSFLLTAVSLSKM (in three-letter code, Phe Leu Leu Trp Ile Leu Ala Ala Val Ser Ser Gly Leu Phe Phe Tyr Ser Phe Leu Leu Thr Ala Val Ser Leu Ser Lys Met).

In another specific embodiment, the PD-1 transmembrane domain of a polypeptide provided herein is or comprises the amino acid sequence (SEQ ID NO: 6)
TLVVGVVGGLLGSLVLLVWVLAVICSRAA (in three-letter code, Thr-Leu-Val-Val-Gly-Val- Val-Gly-Gly-Leu-Leu-Gly-Ser-Leu-Val-Leu-Leu-Val- Trp-Val-Leu-Ala-Val-Ile-Cys-Ser-Arg-Ala-Ala).

In another specific embodiment, the PD-1 transmembrane domain of a polypeptide provided herein is or comprises the amino acid sequence VGVVGGLLGSLVLLVWVLAVI (in three-letter code, Val-Gly-Val-Val-Gly-Gly-Leu-Leu-Gly-Ser-Leu-Val-Leu-Leu-Val-Trp-Val-Leu-Ala-Val-Ile) (SEQ ID NO:7).

In another specific embodiment, the PD-1 transmembrane domain of a polypeptide provided herein is or comprises the amino acid sequence (SEQ ID NO: 8)
FQTLVVGVVGGLLGSLVLLVWVLAVI (in three-letter code, Phe-Gln-Thr-Leu-Val-Val- Gly-Val-Val-Gly-Gly-Leu-Leu-Gly-Ser-Leu-Val-Leu- Leu-Val-Trp-Val-Leu-Ala-Val-Ile).

In another specific embodiment, the PD-1 transmembrane domain of a polypeptide provided herein is or comprises the amino acid sequence (SEQ ID NO: 11)
FQTLVVGVVGGLLGSLVLLVWVLAVICSRAA (in three-letter code, Phe Gln Thr Leu Val Val Gly Val Val Gly Gly Leu Leu Gly Ser Leu Val Leu Leu Val Trp Val Leu Ala Val Ile Cys Ser Arg Ala Ala).

As exemplified by the CTLA-4 and PD-1 transmembrane domain sequences described herein (i.e., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11), the transmembrane domains described herein, in certain embodiments, comprise one or more amino acids from the extracellular domain and/or one or more amino acids from the intracellular domain of the protein from which they are derived (i.e., CTLA-4 or PD-1). In certain embodiments, the transmembrane domains described herein comprise 1, 2, 3, 4, 5, 6, 7, 8, 9, 10, 11, 12, 13, 14, 15, 16, 17, 18, 19, 20, 21, 22, 23, 24, or 25 amino acids from the extracellular domain of the protein from which they are derived (i.e., CTLA-4 or PD-1). In certain embodiments, the transmembrane domains described herein comprise 1, 2, 3, 4, 5, 6, 7, 8, 9, 10, 11, 12, 13, 14, 15, 16, 17, 18, 19, 20, 21, 22, 23, 24, or 25 amino acids from the intracellular domain of the protein from which they are derived (i.e., CTLA-4 or PD-1). In certain embodiments, the transmembrane domains described herein comprise (i) 1, 2, 3, 4, 5, 6, 7, 8, 9, 10, 11, 12, 13, 14, 15, 16, 17, 18, 19, 20, 21, 22, 23, 24, or 25 amino acids from the extracellular domain of the protein from which they are derived (i.e., CTLA-4 or PD-1) and (ii) 1, 2, 3, 4, 5, 6, 7, 8, 9, 10, 11, 12, 13, 14, 15, 16, 17, 18, 19, 20, 21, 22, 23, 24, or 25 amino acids from the intracellular domain of the protein from which they are derived (i.e., CTLA-4 or PD-1).

In another specific embodiment, provided herein is a polypeptide that comprises a transmembrane domain, wherein the transmembrane domain is or comprises at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a polypeptide that comprises a transmembrane domain, wherein the transmembrane domain is at least 75%, at least 80%, at least 85%, at least 90%, or at least 95%, identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In certain embodiments, provided herein is a nucleotide sequence that encodes one of the polypeptides disclosed herein. In a specific embodiment, provided herein is a nucleotide sequence that comprises a nucleotide sequence that encodes any of the amino acid sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a nucleic acid that encodes a polypeptide described herein, wherein the nucleic acid comprises a nucleotide sequence that encodes at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a nucleic acid sequence that encodes a polypeptide that is at least 75%, at least 80%, at least 85%, at least 90%, or at least 95%, identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In constructing the polypeptides provided herein, in certain embodiments, human sequences may be combined with non-human sequences. For example, a polypeptide comprising human extracellular and intracellular domain amino acid sequences may comprise a transmembrane domain from a non-human species; e.g., may comprise a murine CTLA4 transmembrane domain or a murine PD-1 transmembrane domain. In a more specific embodiment, the polypeptide comprises human amino acid sequences for the extracellular and intracellular domains, and comprises a transmembrane domain having, or consisting of, the amino acid sequence of SEQ ID NO:5.

The extracellular domains of the polypeptides provided herein bind to an antigen of interest. In certain embodiments, the extracellular domain of a polypeptide provided herein comprises a receptor, or a portion of a receptor, that binds to said antigen. The extracellular domain may be, e.g., a receptor, or a portion of a receptor, that binds to said antigen. In certain embodiments, the extracellular domain comprises, or is, an antibody or an antigen-binding portion thereof. In specific embodiments, the extracellular domain comprises, or is, a single-chain Fv domain. The single-chain Fv domain can comprise, for example, a $V_L$ linked to $V_H$ by a flexible linker, wherein said $V_L$ and $V_H$ are from an antibody that binds said antigen.

The antigen to which the extracellular domain of the polypeptides provided herein binds/recognizes can be any antigen of interest, e.g., can be an antigen on a tumor cell. The tumor cell may be, e.g., a cell in a solid tumor, or cell of a non-solid tumor, e.g., a cell of a blood cancer. The antigen can be any antigen that is expressed on a cell of any tumor or cancer type, e.g., cells of a lymphoma, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like. In more specific embodiments, said lymphoma can be chronic lymphocytic leukemia (small lymphocytic lymphoma), B-cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma. Antigens specific to certain cancers, as well as methods for identifying such antigens, are known in the art.

In a specific embodiment, in which the cancer is chronic lymphocytic leukemia (CLL), the B cells of the CLL have a normal karyotype. In other specific embodiments, in which the cancer is chronic lymphocytic leukemia (CLL), the B cells of the CLL carry a 17p deletion, an 11q deletion, a 12q trisomy, a 13q deletion or a p53 deletion.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAP1 (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific *enolase* (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein.

In certain embodiments, the TAA or TSA recognized by the extracellular domain of a polypeptide described herein is integrin αvβ3 (CD61), galactin, or Ral-B.

In certain embodiments, the TAA or TSA recognized by the extracellular domain of a polypeptide described herein is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXB1, SPA17, SSX, SYCP1, or TPTE.

In certain other embodiments, the TAA or TSA recognized by the extracellular domain of a polypeptide described herein is a carbohydrate or ganglioside, e.g., fuc-GM1, GM2 (oncofetal antigen-immunogenic-1; OFA-I-1); GD2 (OFA-I-2), GM3, GD3, and the like.

In certain other embodiments, the TAA or TSA recognized by the extracellular domain of a polypeptide described herein is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pmel 17), tyrosinase, TRP-1, TRP-2, MAGE-1, MAGE-3, RAGE, GAGE-1, GAGE-2, p15(58), RAGE, SCP-1, Hom/Mel-40, PRAME, p53, H-Ras, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (Ep-CAM), HTgp-175, M344, MA-50, MG7-Ag, MOV18, NB\70K, NY-CO-1, RCAS1, SDCCAG16, TA-90, TAAL6, TAG72, TLP, or TPS. Other tumor-associated and tumor-specific antigens are known to those in the art.

Antibodies, and scFvs, that bind to TSAs and TAAs are known in the art, as are nucleotide sequences that encode them.

In certain specific embodiments, the antigen recognized by the extracellular domain of a polypeptide described herein is an antigen not considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

In certain embodiments, the extracellular domain of the polypeptides described herein is joined to the transmembrane domain of the polypeptide by a linker, spacer or hinge polypeptide sequence, e.g., a sequence from CD28 or a sequence from CTLA4.

In certain embodiments, the intracellular domain of a polypeptide described herein is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fc receptor subunit or an IL-2 receptor subunit.

In certain embodiments, the polypeptides provided herein additionally comprise one or more co-stimulatory domains or motifs, e.g., as part of the intracellular domain of the polypeptide. The one or more co-stimulatory domains or motifs can be, or comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif.

In a specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CD28 or CTLA4 hinge polypeptide sequence; (iii) a CTLA4 or PD-1 transmembrane domain; (iv) a costimulatory domain; and (v) an intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CH2CH3 hinge polypeptide sequence; (iii) a CTLA4 or PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CD28 hinge polypeptide sequence; (iii) a CTLA4 or PD-1 transmembrane domain; (iv) a 4-1BB costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a PD-1 hinge polypeptide sequence; (iii) a CTLA4 or PD-1 transmembrane domain; (iv) a costimulatory domain; and (v) an intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a PD-1 hinge polypeptide sequence; (iii) a CTLA4 or PD-1 transmembrane domain; (iv) a costimulatory domain; and (v) an intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a CTLA4 transmembrane domain; (iv) a 4-1BB costimulatory domain; and (v) a CD3ζ intracellular signaling domain.

In another specific embodiment, the polypeptide comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a PD-1 transmembrane domain; (iv) a 4-1BB costimulatory domain; and (v) a CD3ζ intracellular signaling domain.

In another specific embodiment, the polypeptide comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a 4-1BB costimulatory domain; and (v) a CD3ζ intracellular signaling domain.

In another specific embodiment, the polypeptide comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a CTLA4 transmembrane domain; (iv) a 4-1BB costimulatory domain; and (v) a CD3ζ intracellular signaling domain.

5.1. Isolated Polypeptides (Chimeric Antigen Receptors)

The T lymphocyte-stimulatory polypeptides provided herein, which comprise a CTLA4 or PD-1 transmembrane domain, may be modified by, e.g., acylation, amidation, glycosylation, methylation, phosphorylation, sulfation, sumoylation, ubiquitylation, or the like. The polypeptides may be labeled with a label capable of providing a detectable signal, e.g., with radioisotopes and fluorescent compounds. One or more side chains of the first or second polypeptides may be derivatized, e.g., derivatization of lysinyl and amino terminal residues with succinic or other carboxylic acid anhydrides, or derivatization with, e.g., imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl)carbodiimide.

5.2. Isolated Nucleic Acids

Provided herein are nucleic acid sequences (polynucleotides) that encode one or more of the polypeptides provided herein. The polynucleotides may be contained within any polynucleotide vector suitable for the transformation of immune cells, e.g., T lymphocytes. For example, T lymphocytes may be transformed using synthetic vectors, lentiviral or retroviral vectors, autonomously replicating plasmids, a virus (e.g., a retrovirus, lentivirus, adenovirus, or herpes virus), or the like, containing polynucleotides encoding the first and second polypeptides (e.g., chimeric receptors). Lentiviral vectors suitable for transformation of T lymphocytes include, but are not limited to, e.g., the lentiviral vectors described in U.S. Pat. Nos. 5,994,136; 6,165,782; 6,428,953; 7,083,981; and 7,250,299, the disclosures of which are hereby incorporated by reference in their entireties. HIV vectors suitable for transformation of T lymphocytes include, but are not limited to, e.g., the vectors described in U.S. Pat. No. 5,665,577, the disclosure of which is hereby incorporated by reference in its entirety.

Nucleic acids useful in the production of the first and second polypeptides, e.g., within a modified T lymphocyte, include DNA, RNA, or nucleic acid analogs. Nucleic acid analogs can be modified at the base moiety, sugar moiety, or phosphate backbone, and can include deoxyuridine substitution for deoxythymidine, 5-methyl-2'-deoxycytidine or 5-bromo-2'-deoxycytidine substitution for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chain. 4:5-23. In addition, the deoxyphosphate backbone can be replaced with, for example, a phosphorothioate or phosphorodithioate backbone, a phosphoroamidite, or an alkyl phosphotriester backbone.

5.3. T Lymphocytes

Provided herein are immune cells, e.g., T lymphocytes, comprising the polypeptides provided herein. The T lymphocytes provided herein may be naive T lymphocytes or MHC-restricted T lymphocytes. In certain embodiments, the T lymphocytes provided herein are tumor infiltrating lymphocytes (TILs). In certain embodiments, the T lymphocytes provided herein have been isolated from a tumor biopsy, or have been expanded from T lymphocytes isolated from a tumor biopsy. In certain other embodiments, the T lymphocytes provided herein have been isolated from, or expanded from, T lymphocytes expanded from, peripheral blood, cord blood, or lymph.

In certain embodiments, the immune cells provided herein that comprise a polypeptide provided herein, e.g., modified T lymphocytes, are autologous to an individual to whom the modified T lymphocytes are to be administered. In certain embodiments, the modified T lymphocytes provided herein are allogeneic to an individual to whom the modified T lymphocytes are to be administered. Where allogeneic T lymphocytes are used to prepare modified T lymphocytes, T lymphocytes can be selected that will reduce the possibility of graft-versus-host disease (GVHD) in the individual. For example, in certain embodiments, virus-specific T lymphocytes can be selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

In one embodiment, T lymphocytes are obtained from an individual, optionally expanded, and then transformed with a polynucleotide encoding a CTLA4 or PD-1 transmembrane domain-containing polypeptide described herein, and optionally expanded. In another embodiment, T lymphocytes are obtained from an individual, optionally then expanded, and then transformed with a polynucleotide encoding a CTLA4 or PD-1 transmembrane domain-containing polypeptide described herein, and optionally then expanded at least one more time. Cells containing the polynucleotides may be selected using a selectable marker.

In certain embodiments, the modified T lymphocytes described herein express or comprise native TCR proteins, e.g., TCR-α and TCR-β that are capable of forming native TCR complexes, in addition to the CTLA4 or PD-1 transmembrane domain-containing polypeptide. In certain other embodiments, either or both of the native genes encoding TCR-α and TCR-β in the modified T lymphocytes are modified to be non-functional, e.g., a portion or all are deleted, a mutation is inserted, etc.

In certain embodiments, the T lymphocytes described herein are isolated from a tumor lesion, e.g., are tumor-infiltrating lymphocytes; such T lymphocytes are expected to be specific for a TSA or TAA.

In certain embodiments, the signaling motifs of the CTLA4 or PD-1 transmembrane domain-containing polypeptide, e.g., CAR, can be used to promote proliferation and expansion of the modified T lymphocytes described herein. For example, unmodified T lymphocytes, and T lymphocytes comprising a polypeptide comprising a CD3ζ signaling domain and a CD28 co-stimulatory domain can be expanded using antibodies to CD3 and CD28, e.g., antibodies attached to beads, or to the surface of a cell culture plate; see, e.g., U.S. Pat. Nos. 5,948,893; 6,534,055; 6,352,694; 6,692,964; 6,887,466; and 6,905,681. In certain embodiments, the antigen, to which the extracellular domain of the CTLA4 or PD-1 transmembrane domain-containing polypeptide binds, can be used to promote selective expansion of T lymphocytes expressing the polypeptide. For example, in one embodiment, in which the antigen is a TSA, T lymphocytes comprising the polypeptide cultured in the presence of the TSA, e.g., a soluble form of the TSA, resulting in increased proliferation as compared to culturing in the absence of the TSA.

In certain embodiments, T lymphocytes comprising a CTLA4 or PD-1 transmembrane domain-containing polypeptide described herein are stimulated to proliferate using an antibody that binds to a signaling domain on the polypeptide coupled with the antigen that can be bound by the extracellular antigen-binding domain of the polypeptide. For example, in embodiments in which the polypeptide's signaling domain is CD3ζ and the antigen that binds to the polypeptide is a TSA, T lymphocytes comprising the polypeptide are stimulated to proliferate by culturing the cells in the presence of the TSA (e.g., a soluble form of the TSA) in combination with an antibody that binds to CD3ζ.

In any of the above embodiments, the antigen and/or antibody can exist free in the medium in which the T lymphocytes are cultures, or either or both can be attached to a solid support, e.g., tissue culture plastic surface, beads, or the like.

The T lymphocytes comprising a CTLA4 or PD-1 transmembrane domain-containing polypeptide described herein can optionally comprise a "suicide gene" or "safety switch" that enables killing of all or substantially all of the T lymphocytes when desired. For example, the modified T lymphocytes described herein, in certain embodiments, can comprise an HSV thymidine kinase gene (HSV-TK), which causes death of the modified T lymphocytes upon contact with gancyclovir. In another embodiment, the modified T lymphocytes express or comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 105(11):4247-4254 (2005).

5.4. Methods of Using Modified T Lymphocytes

The modified immune cells, e.g., the modified T lymphocytes, provided herein that comprise a CTLA4 or PD-1 transmembrane domain-containing polypeptide, e.g., CAR, can be used to treat an individual having one or more types of cells desired to be targeted by T lymphocytes, e.g., one or more types of cells to be killed. In certain embodiments, the cells to be killed are cancer cells, e.g., tumor cells. In certain embodiments, the cancer cells are cells of a solid tumor. In certain embodiments, the cells are cells of a lymphoma, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like. In more specific embodiments, said lymphoma can be chronic lymphocytic leukemia (small lymphocytic lymphoma), B-cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

Efficacy of the modified T lymphocytes described herein, after administration to an individual having a disease or disorder remediable by T lymphocytes, e.g., an individual having cancer, can be assessed by one or more criteria, specific to the particular disease or disorder, known to those of ordinary skill in the art, to be indicative of progress of the disease or disorder. Generally, administration of the modified T lymphocytes described herein to such an individual is effective when one or more of said criteria detectably, e.g., significantly, moves from a disease state value or range to, or towards, a normal value or range.

The modified T lymphocytes described herein may be formulated in any pharmaceutically-acceptable solution, preferably a solution suitable for the delivery of living cells, e.g., saline solution (such as Ringer's solution), gelatins, carbohydrates (e.g., lactose, amylose, starch, or the like), fatty acid esters, hydroxymethylcellulose, polyvinyl pyrolidine, etc. Such preparations are preferably sterilized prior to addition of the modified T lymphocytes, and may be mixed with auxiliary agents such as lubricants, preservatives, stabilizers, emulsifiers, salts for influencing osmotic pressure, buffers, and coloring. Pharmaceutical carriers suitable for use in formulating the modified T lymphocytes are known in the art and are described, for example, in WO 96/05309.

In certain embodiments, the modified T lymphocytes described herein are formulated into individual doses, wherein said individual doses comprise at least, at most, or about $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, or $1 \times 10^{11}$ modified T lymphocytes. In certain embodiments, the modified T lymphocytes are formulated for intravenous, intraarterial, parenteral, intramuscular, subcutaneous, intrathecal, or intraocular administration, or administration within a particular organ or tissue.

6. EXAMPLES

6.1. Example 1

Treatment of B Cell Lymphoma

An individual presents with B-cell chronic lymphocytic leukemia, a B cell lymphoma. Testing of B cells from the individual determines that the B cells carry a 17p deletion. T lymphocytes are obtained from the individual, transfected with a lentiviral vector comprising a nucleotide sequence that encodes a chimeric antigen receptor (CAR), and expanded using CD3+CD28-coated beads to sufficient numbers for administration. The chimeric receptor comprises an extracellular antigen-binding region that binds to CD19; a transmembrane domain from CTLA4; an intracellular costimulatory domain from CD28; and an intracellular CD3ζ domain. The individual is administered between $10^9$ and $10^{10}$ of the T lymphocytes in a 200 ml saline solution by intravenous infusion over 30 minutes. The individual is monitored for two weeks afterwards to establish a reduction of at least 90% of CD19+ B cells in the individual's blood.

6.2. Example 2

Treatment of a B Cell Lymphoma

An individual presents with B-cell chronic lymphocytic leukemia, a B cell lymphoma. Testing of B cells from the individual determines that the B cells carry a 17p deletion. About $10^6$ T lymphocytes are obtained from the individual, transfected with a lentiviral vector comprising a nucleotide sequence that encodes a CAR. The CAR comprises an extracellular antigen-binding region that binds to CD19; a transmembrane domain from PD-1; an intracellular costimulatory domain from CD28; and an intracellular CD3ζ domain. CAR-expressing T cells are administered to the individual without prior expansion of the T cells. The individual is administered between $10^5$ and $10^6$ of the T lymphocytes in 200 ml saline solution by intravenous infusion over 30 minutes. The individual is monitored for two weeks afterwards to establish a reduction of at least 90% of CD19+ B cells in the individual's blood.

6.3. Example 3

Treatment of B Cell Lymphoma

An individual presents with B-cell chronic lymphocytic leukemia, a B cell lymphoma. Testing of B cells from the individual determines that the B cells carry a p53 deletion. T lymphocytes are obtained from the individual, transfected with a lentiviral vector comprising a nucleotide sequence that encodes a CAR, and expanded using CD3+CD28-coated beads to sufficient numbers for administration. The CAR comprises an extracellular antigen-binding region that binds to CD19; a transmembrane domain from CTLA4; intracellular co-stimulatory domains from each of CD28, 4-1BB, and OX40; and an intracellular CD3ζ domain. The individual is administered between $10^9$ and $10^{10}$ of the T lymphocytes in 200 ml saline solution by intravenous infusion over 30 minutes. The individual is monitored for two weeks afterwards to establish a reduction of at least 90% of CD19+ B cells in the individual's blood.

6.4. Example 4

Treatment of a B Cell Lymphoma

An individual presents with B-cell chronic lymphocytic leukemia, a B cell lymphoma. Testing of B cells from the individual determines that the B cells carry a p53 deletion. About $10^6$ T lymphocytes are obtained from the individual, transfected with a lentiviral vector comprising a nucleotide sequence that encodes a CAR. The CAR comprises an extracellular antigen-binding region that binds to CD19; a transmembrane domain from PD-1; intracellular co-stimulatory domains from each of CD28, 4-1BB, and OX40; and an intracellular CD3ζ domain. CAR-expressing T cells are administered to the individual without prior expansion of the T cells. The individual is administered between $10^5$ and $10^6$ of the T lymphocytes in 200 ml saline solution by intravenous infusion over 30 minutes. The individual is monitored for two weeks afterwards to establish a reduction of at least 90% of CD19+ B cells in the individual's blood.

6.5. Example 5

Treatment of Prostate Cancer

An individual presents with stage T2 prostate cancer, with no spread to regional or other lymph nodes (N0, M0). Histological grade is determined to be G2. Overall, the individual is determined to have Stage I1 prostate cancer. The individual is administered between $10^9$ and $10^{10}$ modified T lymphocytes that comprise a CAR, in 200 ml saline solution by intravenous infusion over 30 minutes. The CAR comprises an extracellular antigen-binding region that binds to PSCA, a transmembrane domain from CTLA4, an intracellular co-stimulatory domain from CD28, and an intracellular CD3ζ domain. The individual is re-assessed for prostate cancer stage and spread to lymph nodes, and histology of biopsied prostate tissue is performed, at 30, 60 and 90 days post-administration.

6.6. Example 6

Treatment of Prostate Cancer

An individual presents with stage T2 prostate cancer, with no spread to regional or other lymph nodes (N0, M0). Histological grade is determined to be G2. Overall, the individual is determined to have Stage I1 prostate cancer. The individual is administered between $10^9$ and $10^{10}$ modified T lymphocytes that comprise a CAR, in 200 ml saline solution by intravenous infusion over 30 minutes. The CAR comprises an extracellular antigen-binding region that binds to PSCA, a transmembrane domain from PD-1, an intracellular co-stimulatory domain from CD28, and an intracellular CD3ζ domain. The individual is re-assessed for prostate cancer stage and spread to lymph nodes, and histology of biopsied prostate tissue is performed, at 30, 60 and 90 days post-administration.

6.7. Example 7

Treatment of Prostate Cancer

An individual presents with stage T2 prostate cancer, with no spread to regional or other lymph nodes (N0, M0). Histological grade is determined to be G2. Overall, the individual is determined to have Stage I1 prostate cancer. The individual is administered between $10^9$ and $10^{10}$ modified T lymphocytes that comprise a CAR, in 200 ml saline solution by intravenous infusion over 30 minutes. The CAR comprises an extracellular antigen-binding region that binds to PSCA, a transmembrane domain from CTLA-4, intracellular co-stimulatory domains from each of CD28, 4-1BB, and OX40, and an intracellular CD3ζ domain. The individual is re-assessed for prostate cancer stage and spread to lymph nodes, and histology of biopsied prostate tissue is performed, at 30, 60 and 90 days post-administration.

6.8. Example 8

Treatment of Prostate Cancer

An individual presents with stage T2 prostate cancer, with no spread to regional or other lymph nodes (N0, M0). Histological grade is determined to be G2. Overall, the individual is determined to have Stage I1 prostate cancer. The individual is administered between $10^9$ and $10^{10}$ modified T lymphocytes that comprise a CAR, in 200 ml saline solution by intravenous infusion over 30 minutes. The CAR comprises an extracellular antigen-binding region that binds to PSCA, a transmembrane domain from PD-1, intracellular co-stimulatory domains from each of CD28, 4-1BB, and OX40, and an intracellular CD3ζ domain. The individual is re-assessed for prostate cancer stage and spread to lymph nodes, and histology of biopsied prostate tissue is performed, at 30, 60 and 90 days post-administration.

6.9. Example 9

CARs Comprising a CTLA-4 or PD-1 Transmembrane Domain

This example demonstrates that a chimeric antigen receptor comprising a CTLA-4 or PD-1 transmembrane domain is functional and active in T cells.

6.9.1 CARs Comprising a CTLA-4 Transmembrane Domain

CARs comprising an extracellular domain (anti-HER2 scFV) that binds the antigen HER2 were generated. Specifically, the following CARs were generated: (i) HER-28TMζ, comprising an Anti-HER2 scFV, a CD28 transmembrane domain, and a CD3ζ intracellular domain; (ii) HER-28TM28ζ, comprising an Anti-HER2 scFV, a CD28 transmembrane domain, and a CD28-CD3ζ intracellular domain; (iii) HER2-CTLA4TM28ζ, comprising an Anti-HER2 scFV, a CH2CH3 hinge, a CTLA-4 transmembrane domain (SEQ ID NO:10), and a CD28-CD3ζ intracellular domain; and (iv) HER2-41BBTM28ζ, comprising an Anti-HER2 scFV, a CD8 hinge, a 4-1BB transmembrane domain, and a CD28-CD3ζ intracellular domain.

The ability of human T cells to express the CARs described above was assessed. Pan T cells and naïve Pan T cells were isolated from buffy coat of donor sample blood by negative selection using a human Pan T isolation Kit II and human naïve Pan T isolation kit, respectively (Miltenyi, Cambridge, Mass.). Isolated T cells were cultured in RPMI complete media in the presence of 10 ng/ml IL-7 for 11 days, and then transduced with lentivirus expressing CAR constructs at MOI of 5.

Three days after transduction, CAR T cell phenotype was characterized staining the cells with a HER2-Fc fusion protein (R&D Systems, Minneapolis, Minn.), followed by staining with a polyclonal goat anti-human IgG-Fc antibody conjugated with FITC or APC) (Jackson ImmunoResseach, West Grove, Pa.). On the same day, T cells were stimulated with HER2-Fc fusion protein at a gradient of concentrations ranging from 0.25 μg/ml to 1 μg/ml. Supernatant was collected 48 hours post-stimulation for cytometric beads array (CBA) analysis, to assess cytokine production by the T cells, using a customized CBA flex set (BD Biosciences, San Jose, Calif.). The cells from the culture after supernatant removal were stained for measurement of T cell activation surface markers CD69, 4-1BB, CD71, HLA-DR, and CD25 using anti-human monoclonal antibodies with fluorochrome conjugates (BD Biosciences). Flow cytometric analysis for both CBA and surface markers was performed on a FACS Canto II machine and data were acquired with FACSDiva software (BD Biosciences). The CBA data were analyzed with FCAP Assay software (Soft Flow Ltd., Pecs, Hungary). Surface marker flow data were analyzed using FlowJo flow cytometry software (Tree Star, Ashland, Oreg.).

Figure 1:
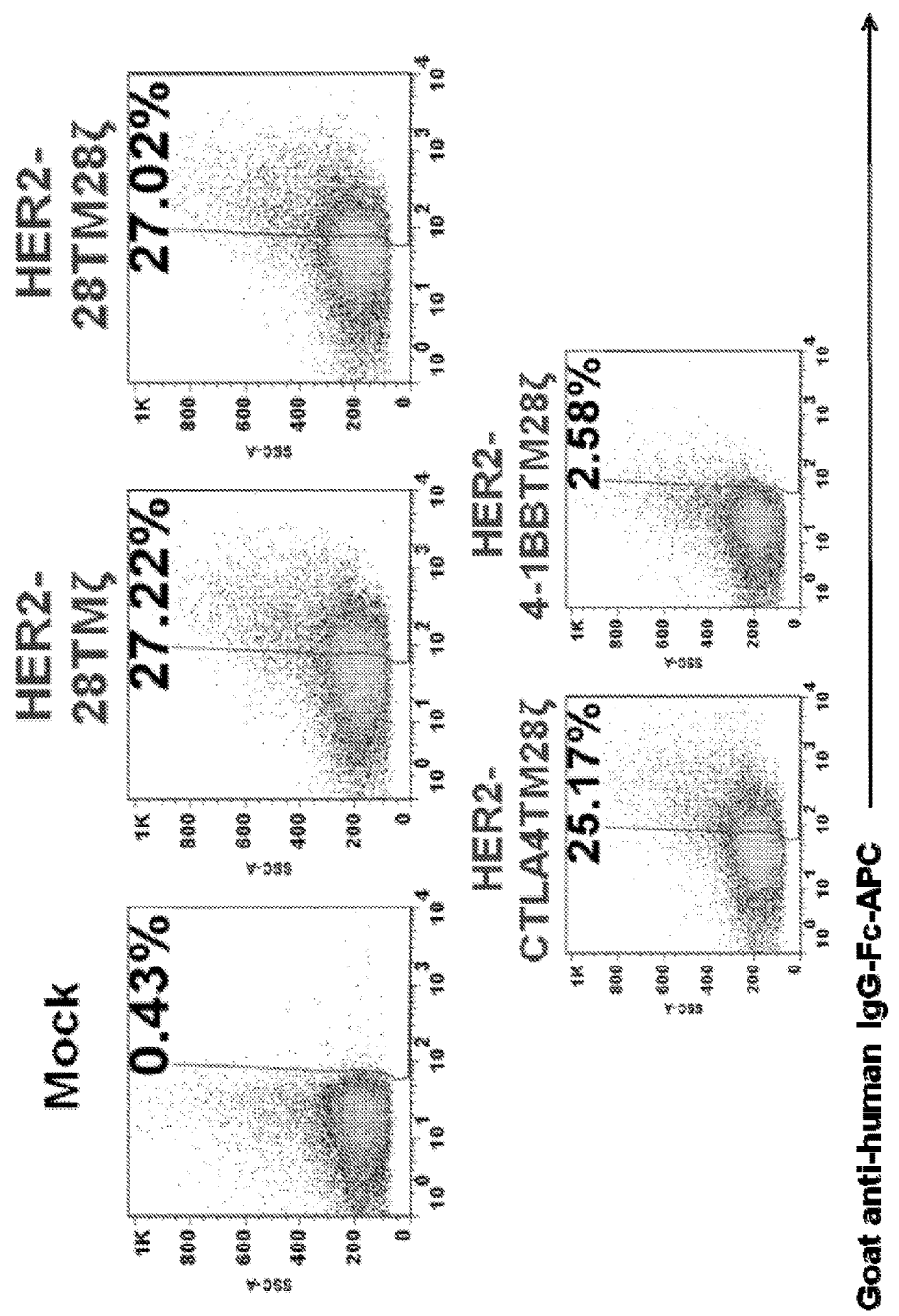
FIG. 1 depicts expression of CARs by T cells three days after transduction of the T cells with lentiviral vectors that express the CARS.

As shown in FIG. 1, three of the CARs generated, including the CAR having a CTLA-4 transmembrane domain, were highly expressed by the T cells. T cell activation surface markers CD69, 4-1BB, and HLA-DR each were upregulated upon CAR ligation, i.e., when the CAR T cells were stimulated with HER2-Fc fusion protein. In each case, the highest levels were observed in CAR T cells expressing the construct HER2-CTLA4TM28ζ.

Figure 2:
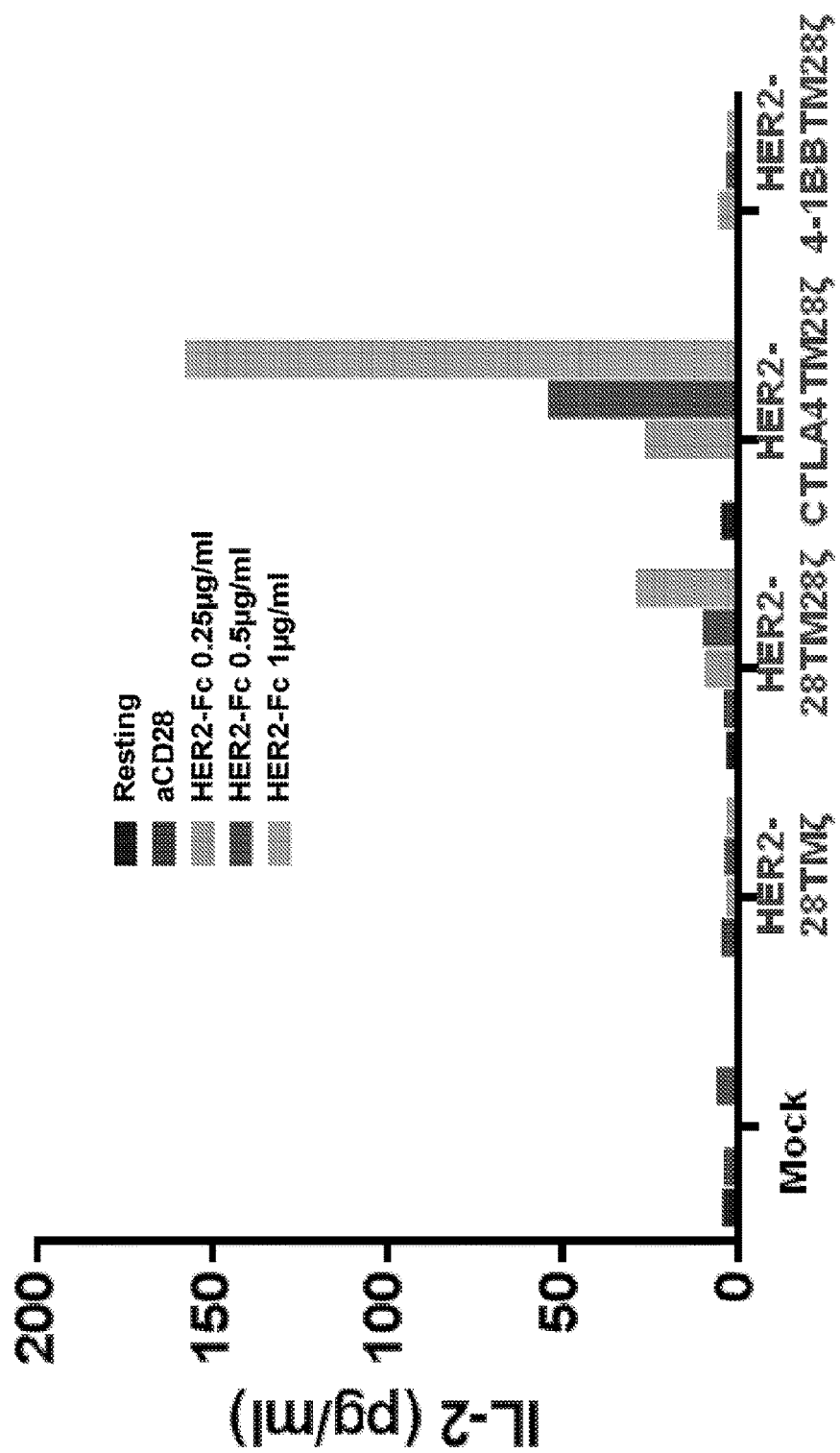
FIG. 2 depicts interleukin-2 (IL-2) production by CAR T cells (i) in the resting state (first bar), (ii) after exposure to anti-CD28 (second bar); (iii) after exposure to 0.25 µg/ml HER2-Fc; (iv) after exposure to 0.5 µg/ml HER2-Fc; and (v) after exposure to 1.0 µg/ml HER2-Fc.
Figure 3:
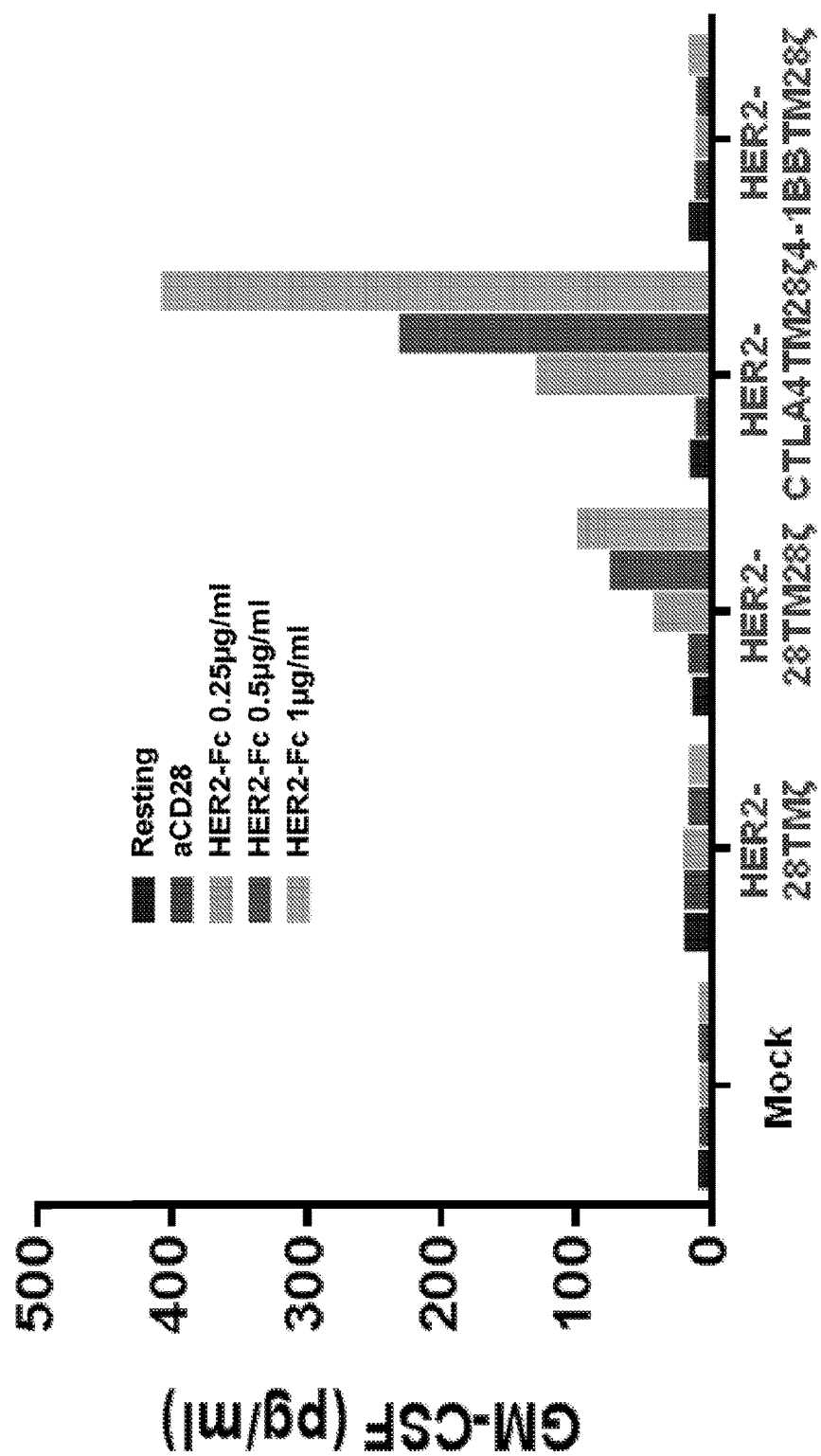
FIG. 3 depicts GM-CSF production by CAR T cells (i) in the resting state (first bar), (ii) after exposure to aCD28 (second bar); (iii) after exposure to 0.25 µg/ml HER2-Fc; (iv) after exposure to 0.5 µg/ml HER2-Fc; and (v) after exposure to 1.0 µg/ml HER2-Fc.
Figure 4:
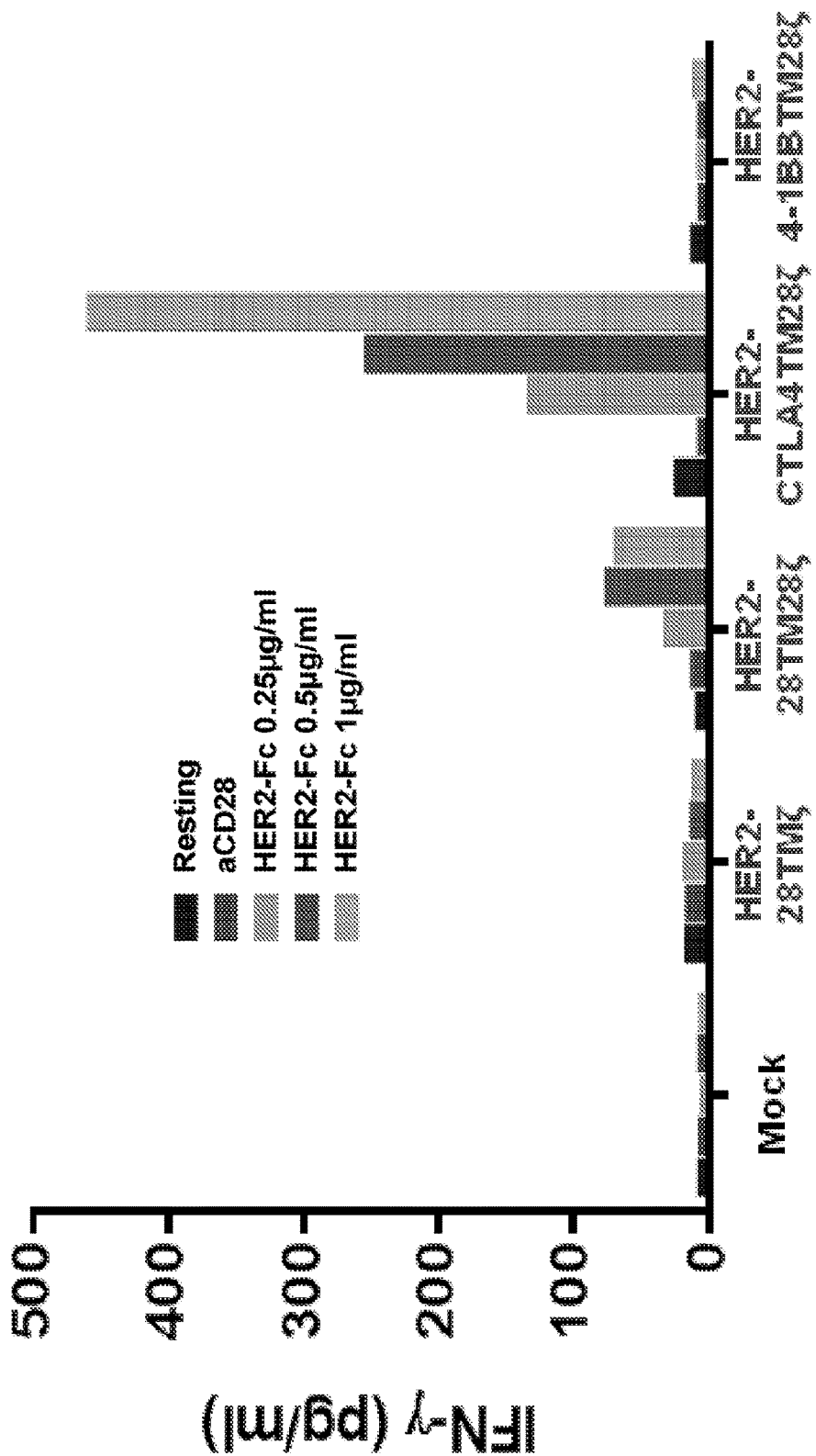
FIG. 4 depicts interferon-gamma (IFN-γ) production by CAR T cells (i) in the resting state (first bar), (ii) after exposure to aCD28 (second bar); (iii) after exposure to 0.25 µg/ml HER2-Fc; (iv) after exposure to 0.5 µg/ml HER2-Fc; and (v) after exposure to 1.0 µg/ml HER2-Fc.

As shown in FIGS. 2-4, two of the four sets of CAR T cells demonstrated cytokine production in response to HER2 stimulation. Specifically, T cells expressing the CAR designated HER2-28TM28ζ and T cells expressing the CAR designated HER2-CTLA4TM28ζ produced the cytokines interleukin-2 (IL-2) (FIG. 2), GM-CSF (FIG. 3), and interferon-gamma (IFN-γ) (FIG. 4) in a dose-dependent manner in response to HER2 stimulation. Surprisingly, T cells expressing a CAR comprising a transmembrane domain from a protein that normally transmits an inhibitory signal to immune system cells (i.e., CTLA-4 transmembrane domain) produced a much higher level of each cytokine as compared to T cells expressing each of the other CARs, including T cells expressing the CAR designated HER2-28TM28ζ. See FIGS. 2-4.

Figure 5:
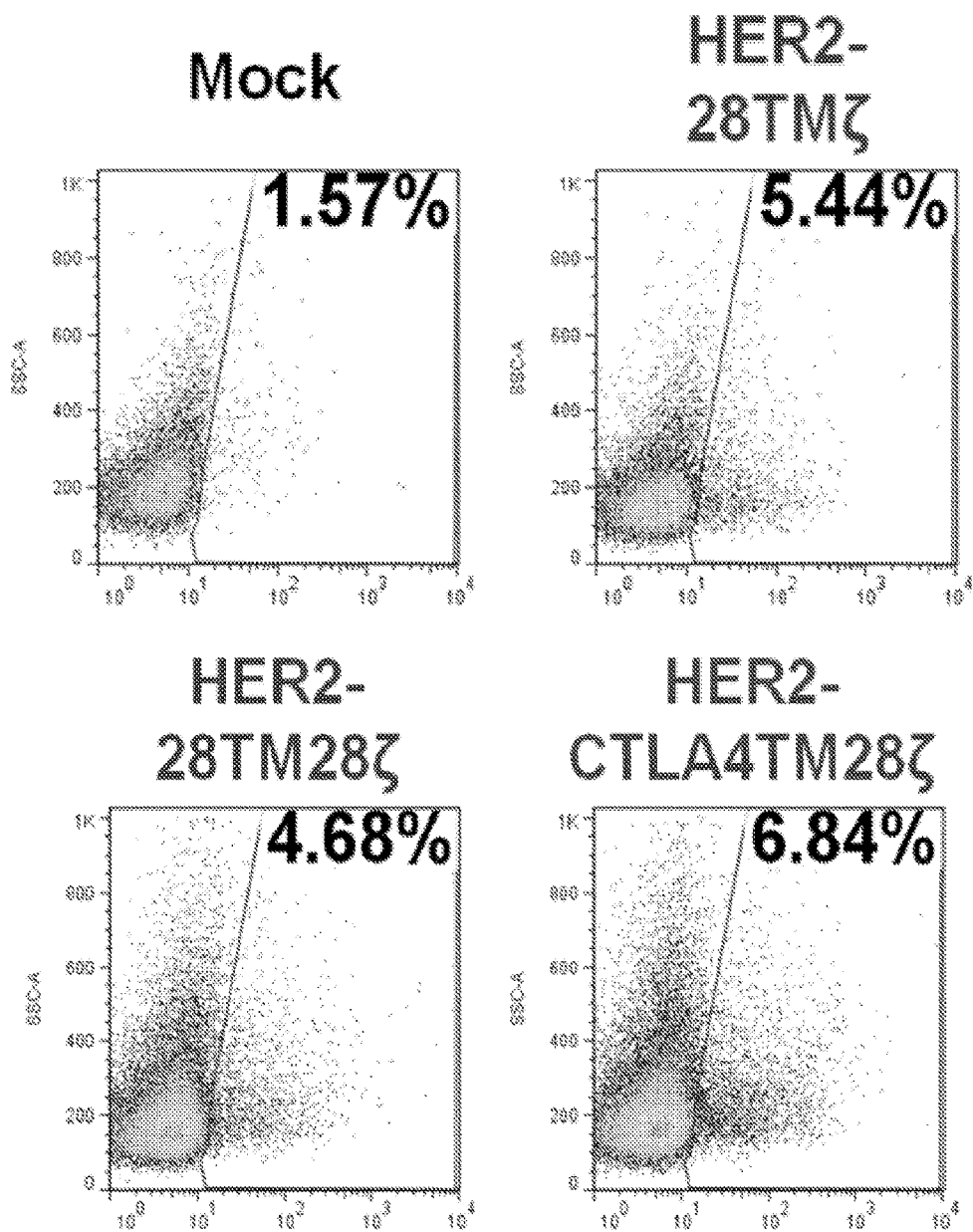
FIG. 5 depicts intracellular tumor necrosis factor alpha (TNF-α) production by CAR T cells after multiple rounds of exposure to 1.0 µg/ml HER2-Fc.

It further was examined whether stimulation of T cells expressing the CARs described above with HER2 induces intracellular tumor necrosis factor-alpha (TNF-α) production by the T cells. The CAR T cells were stimulated with HER2-Fc (1 μg/ml) for 2 days in medium containing IL-2 (50 IU/ml). The HER2 stimulation was performed two more times, separated by seven days each time. After the third stimulation, intracellular TNF-α was examined by flow cytometry. As shown in FIG. 5, T cells expressing the CAR designated HER2-28TM28ζ, T cells expressing the CAR designated HER2-CTLA4TM28ζ, and T cells expressing the CAR designated HER2-28TMζ produced TNF-α, with the highest amount of TNF-α produced by T cells expressing a CAR comprising a transmembrane domain from a protein that normally transmits an inhibitory signal to immune system cells (i.e., CTLA-4 transmembrane domain).

Finally, it was determined whether stimulation of T cells expressing the CARs described above with HER2 results in enrichment of the CAR T cell populations. CAR T cells expressing the CARs described above were stimulated with HER2-Fc fusion protein. Thirteen days post-stimulation with HER2, CAR T cells were analyzed by flow cytometry, as described above. Surprisingly, as shown in FIG. 6, only CAR T cells expressing the CAR designated HER2-CTLA4TM28ζ were enriched following HER2 stimulation.

6.9.2 CARs Comprising a PD-1 or CTLA-4 Transmembrane Domain

This example demonstrates that a chimeric antigen receptor comprising a CTLA-4 transmembrane domain or a PD-1 transmembrane domain is functional and active in T cells.

CARs comprising an extracellular domain (anti-HER2 scFV) that binds the antigen HER2 were generated. Specifically, the following CARs were generated: (i) HER-PD1TM-CD28-CD3, comprising an Anti-HER2 scFV, a CH2CH3 hinge, a PD-1 transmembrane domain (SEQ ID NO:11), and a CD28-CD3 intracellular domain; (ii) HER-CTLA4(189)TM-41BB-CD3, comprising an Anti-HER2 scFV, a CD28 hinge, a CTLA-4 transmembrane domain (SEQ ID NO:10), and a 4-1BB-CD3 intracellular domain; (iii) HER-PD1TM-41BB-CD3, comprising an Anti-HER2 scFV, a CD28 hinge, a PD-1 transmembrane domain (SEQ ID NO:11), and a 4-1BB-CD3 intracellular domain; and (iv) HER2-CD28TM-CD28-CD3, comprising an Anti-HER2 scFV, a CD28 hinge, a CD28 transmembrane domain, and a CD28-CD3 intracellular domain.

Pan T cells and naïve Pan T cells were isolated from buffy coat of donor sample blood by negative selection using a human Pan T isolation Kit II and human naïve Pan T isolation kit, respectively (Miltenyi, Cambridge, Mass.). Isolated T cells were cultured in RPMI complete media in the presence of 10 ng/ml IL-7 for 11 days, and then transduced with lentivirus expressing CAR constructs at MOI of 7.

Three days after transduction, CAR T cell phenotype was characterized staining the cells with a HER2-Fc fusion protein (R&D Systems, Minneapolis, Minn.), followed by staining with a polyclonal goat anti-human IgG-Fc antibody conjugated with FITC or APC) (Jackson ImmunoResseach, West Grove, Pa.). On the same day, T cells were stimulated with HER2-Fc fusion protein at a gradient of concentrations ranging from 0.25 μg/ml to 1 μg/ml. Supernatant was collected 48 hours post-stimulation for cytometric beads array (CBA) analysis, to assess cytokine production by the T cells, using a customized CBA flex set (BD Biosciences, San Jose, Calif.). The cells from the culture after supernatant removal were stained for measurement of T cell activation surface markers CD69, 4-1BB, CD71, HLA-DR, and CD25 using anti-human monoclonal antibodies with fluorochrome conjugates (BD Biosciences). Flow cytometric analysis for both CBA and surface markers was performed on a FACS Canto II machine and data were acquired with FACSDiva software (BD Biosciences). The CBA data were analyzed with FCAP Assay software (Soft Flow Ltd., Pecs, Hungary). Surface marker flow data were analyzed using FlowJo flow cytometry software (Tree Star, Ashland, Oreg.).

As shown in FIG. 7, each of the CARs generated were highly expressed by the T cells. T cell activation surface markers CD69, CD71, and HLA-DR each were upregulated upon stimulation of the above-described CAR T cells with HER2. In each case, the observed levels of upregulation were highest in CAR T cells expressing CARs with either a PD-1 or a CTLA-4 transmembrane domain.

As shown in FIGS. 8-9, the CAR T cells demonstrated cytokine production in response to HER2 stimulation. Specifically, T cells expressing the CARs described above produced the cytokines IL-2 (FIG. 8), TNF-α (FIG. 8), and IFN-γ (FIG. 8), GM-CSF (FIG. 9), Granzyme B (FIG. 9), and IL-13 (FIG. 9) in a dose-dependent manner in response to HER2 stimulation. In each case, T cells expressing CARs comprising a PD-1 or CTLA-4 transmembrane domain exhibited the highest levels of cytokine production, with T cells expressing the CAR designated HER-PD1TM-CD28-CD3 consistently producing the highest levels of each cytokine (see FIGS. 8 and 9).

Finally, it was determined whether stimulation of T cells expressing the CARs described above with HER2 results in enrichment of the CAR T cell populations. CAR T cells expressing the CARs described above were stimulated with HER2-Fc fusion protein. Eleven days post-stimulation with HER2, CAR T cells were analyzed by flow cytometry, as described above. As shown in FIG. 10, CAR T cells expressing the CAR designated HER-PD1TM-CD28-CD3 were enriched following HER2 stimulation, with T cells expressing the other CARs described showing modest levels of increase in live cells over the initial cell number.

6.9.3 Conclusion

In conclusion, generation of T cells expressing a CAR that comprises a transmembrane domain from a protein that normally transmits an inhibitory signal to immune system cells has been demonstrated. Further, it has been shown that such CAR T cells possess surprising characteristics. In particular, such T cells (i) demonstrate elevated levels of cytokine production in response to stimulation with the antigen to which the extracellular domain of the CAR they express is directed, as compared to T cells expressing CARs that comprise a transmembrane domain from a protein that normally transmits a stimulatory signal to immune system cells; and (ii) are enriched when cultured in the presence of the antigen to which the extracellular domain of the CAR they express is directed, whereas T cells expressing CARs that comprise a transmembrane domain from a protein that normally transmits a stimulatory signal to immune system cells are not enriched to the same extent, when stimulated with the antigen.

EQUIVALENTS

The present disclosure is not to be limited in scope by the specific embodiments described herein. Indeed, various modifications of the subject matter provided herein, in addition to those described, will become apparent to those skilled in the art from the foregoing description. Such modifications are intended to fall within the scope of the appended claims.

Various publications, patents and patent applications are cited herein, the disclosures of which are incorporated by reference in their entireties.

What is claimed is:

1. A polypeptide comprising (i) a transmembrane domain from PD-1, (ii) a CD3ζ intracellular signaling domain, and (iii) an extracellular domain that binds to an antigen on a tumor cell, wherein said extracellular domain is an antibody or an antigen-binding portion thereof, and wherein the intracellular domain and the extracellular domain of said polypeptide are not from PD-1, wherein said polypeptide, when expressed on the surface of a T lymphocyte, directs the T lymphocyte to kill a cell expressing said antigen.

2. The polypeptide of claim 1, wherein said polypeptide is a chimeric antigen receptor (CAR).

3. The polypeptide of claim 1, wherein a T lymphocyte expressing said polypeptide is stimulated to proliferate when said polypeptide binds to said antigen.

4. The polypeptide of claim 1, wherein said antigen is a tumor-associated antigen or a tumor-specific antigen.

5. The polypeptide of claim 4, wherein said tumor-associated antigen or tumor-specific antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, an abnormal p53 protein, integrin av$\beta$3 (CD61), galactin, K-Ras (V-Ki-ras2 Kirsten rat sarcoma viral oncogene), or Ral-B.

6. The polypeptide of claim 1, wherein said polypeptide additionally comprises one or more co-stimulatory domains, wherein said one or more co-stimulatory domains comprises one or more of: a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, and a co-stimulatory inducible T-cell costimulatory (ICOS) polypeptide sequence.

7. The polypeptide of claim 1, wherein said polypeptide comprises, in order, from N-terminus to C terminus: (i) the extracellular domain that binds to an antigen on a tumor cell; (ii) a hinge polypeptide sequence from CD28 or CTLA4; (iii) the transmembrane domain from PD-1; (iv) a costimulatory domain; and (v) the CD3$\zeta$ intracellular signaling domain.

8. The polypeptide of claim 7, wherein said polypeptide comprises, in order, from N-terminus to C-terminus: (i) a single-chain Fv domain comprising a $V_L$ linked to $V_H$ by a flexible linker, wherein said $V_L$ and $V_H$ are from an antibody that binds said antigen; (ii) a hinge polypeptide sequence from CD28; (iii) the transmembrane domain from PD-1; (iv) a CD28 costimulatory domain; and (v) the CD3$\zeta$ intracellular signaling domain.

9. The polypeptide of claim 7, wherein said polypeptide comprises, in order, from N-terminus to C-terminus: (i) a single-chain Fv domain comprising a $V_L$ linked to $V_H$ by a flexible linker, wherein said $V_L$ and $V_H$ are from an antibody that binds said antigen; (ii) a hinge polypeptide sequence from CTLA4; (iii) the transmembrane domain from PD-1; (iv) a CD28 costimulatory domain; and (v) the CD3$\zeta$ intracellular signaling domain.

10. A T lymphocyte comprising the polypeptide of claim 1.

* * * * *

```
SEQUENCE LISTING

<160> NUMBER OF SEQ ID NOS: 11

<210> SEQ ID NO 1
<211> LENGTH: 36
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 1

Pro Glu Pro Cys Pro Asp Ser Asp Phe Leu Leu Trp Ile Leu Ala Ala
1               5                   10                  15

Val Ser Ser Gly Leu Phe Phe Tyr Ser Phe Leu Leu Thr Ala Val Ser
            20                  25                  30

Leu Ser Lys Met
        35

<210> SEQ ID NO 2
<211> LENGTH: 29
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 2

Pro Asp Ser Asp Phe Leu Leu Trp Ile Leu Ala Ala Val Ser Ser Gly
1               5                   10                  15

Leu Phe Phe Tyr Ser Phe Leu Leu Thr Ala Val Ser Leu
            20                  25

<210> SEQ ID NO 3
<211> LENGTH: 23
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 3
```

Phe Leu Leu Trp Ile Leu Ala Ala Val Ser Ser Gly Leu Phe Phe Tyr
1               5                   10                  15

Ser Phe Leu Leu Thr Ala Val
            20

<210> SEQ ID NO 4
<211> LENGTH: 21
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 4

Phe Leu Leu Trp Ile Leu Ala Ala Val Ser Ser Gly Leu Phe Phe Tyr
1               5                   10                  15

Ser Phe Leu Leu Thr
            20

<210> SEQ ID NO 5
<211> LENGTH: 26
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 5

Phe Leu Leu Trp Ile Leu Val Ala Val Ser Leu Gly Leu Phe Phe Tyr
1               5                   10                  15

Ser Phe Leu Val Ser Ala Val Ser Leu Ser
            20                  25

<210> SEQ ID NO 6
<211> LENGTH: 29
<212> TYPE: PRT
<213> ORGANISM: Artificial Sequence
<220> FEATURE:
<223> OTHER INFORMATION: synthetic peptide - PD-1 transmembrane domain

<400> SEQUENCE: 6

Thr Leu Val Val Gly Val Val Gly Gly Leu Leu Gly Ser Leu Val Leu
1               5                   10                  15

Leu Val Trp Val Leu Ala Val Ile Cys Ser Arg Ala Ala
            20                  25

<210> SEQ ID NO 7
<211> LENGTH: 21
<212> TYPE: PRT
<213> ORGANISM: Artificial Sequence
<220> FEATURE:
<223> OTHER INFORMATION: synthetic peptide - PD-1 transmembrane domain

<400> SEQUENCE: 7

Val Gly Val Val Gly Gly Leu Leu Gly Ser Leu Val Leu Leu Val Trp
1               5                   10                  15

Val Leu Ala Val Ile
            20

<210> SEQ ID NO 8
<211> LENGTH: 26
<212> TYPE: PRT
<213> ORGANISM: Artificial Sequence
<220> FEATURE:
<223> OTHER INFORMATION: synthetic peptide - PD-1 transmembrane domain

```
<400> SEQUENCE: 8

Phe Gln Thr Leu Val Val Gly Val Val Gly Gly Leu Leu Gly Ser Leu
1               5                   10                  15

Val Leu Leu Val Trp Val Leu Ala Val Ile
            20                  25

<210> SEQ ID NO 9
<211> LENGTH: 49
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 9

Leu Gly Ile Gly Asn Gly Thr Gln Ile Tyr Val Ile Asp Pro Glu Pro
1               5                   10                  15

Ser Pro Asp Ser Asp Phe Leu Leu Trp Ile Leu Ala Ala Val Ser Ser
            20                  25                  30

Gly Leu Phe Phe Tyr Ser Phe Leu Leu Thr Ala Val Ser Leu Ser Lys
        35                  40                  45

Met

<210> SEQ ID NO 10
<211> LENGTH: 28
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 10

Phe Leu Leu Trp Ile Leu Ala Ala Val Ser Ser Gly Leu Phe Phe Tyr
1               5                   10                  15

Ser Phe Leu Leu Thr Ala Val Ser Leu Ser Lys Met
            20                  25

<210> SEQ ID NO 11
<211> LENGTH: 31
<212> TYPE: PRT
<213> ORGANISM: Artificial Sequence
<220> FEATURE:
<223> OTHER INFORMATION: synthetic peptide - PD-1 transmembrane domain

<400> SEQUENCE: 11

Phe Gln Thr Leu Val Val Gly Val Val Gly Gly Leu Leu Gly Ser Leu
1               5                   10                  15

Val Leu Leu Val Trp Val Leu Ala Val Ile Cys Ser Arg Ala Ala
            20                  25                  30
```